(12) United States Patent
Nakabayashi

(10) Patent No.: US 12,656,538 B2
(45) Date of Patent: Jun. 16, 2026

(54) BLAZED DIFFRACTIVE OPTICAL ELEMENT AND METHOD OF MANUFACTURING BLAZED DIFFRACTIVE OPTICAL ELEMENT

(71) Applicant: FUJIFILM CORPORATION, Tokyo (JP)

(72) Inventor: Koki Nakabayashi, Saitama (JP)

(73) Assignee: FUJIFILM CORPORATION, Tokyo (JP)

( * ) Notice: Subject to any disclaimer, the term of this patent is extended or adjusted under 35 U.S.C. 154(b) by 609 days.

(21) Appl. No.: 18/060,967

(22) Filed: Dec. 2, 2022

(65) Prior Publication Data

US 2023/0104387 A1 Apr. 6, 2023

Related U.S. Application Data

(63) Continuation of application No. PCT/JP2021/021755, filed on Jun. 8, 2021.

(30) Foreign Application Priority Data

Jun. 30, 2020 (JP) ................................. 2020-113523

(51) Int. Cl.
*G02B 5/18* (2006.01)
*A61F 2/16* (2006.01)
(52) U.S. Cl.
CPC .......... *G02B 5/1857* (2013.01); *A61F 2/1654* (2013.01); *A61F 2250/0026* (2013.01)
(58) Field of Classification Search
CPC ...... G02B 5/1857; G02B 3/08; G02B 5/1814; G02B 5/1876; A61F 2/1654;

(Continued)

(56) References Cited

U.S. PATENT DOCUMENTS 4,944,584 A * 7/1990 Maeda ..................... G02C 7/06
351/159.48
10,531,950 B2 * 1/2020 Tiwari .................. A61F 2/1618
(Continued)

FOREIGN PATENT DOCUMENTS

EP 2820465 B1 * 11/2019 ......... G02B 27/0093
JP 2006-072169 A 3/2006
(Continued)

OTHER PUBLICATIONS

International Search Report issued in International Application No. PCT/JP2021/021755 on Aug. 31, 2021.
(Continued)

*Primary Examiner* — Thomas K Pham
*Assistant Examiner* — Ruby L Kauffman
(74) *Attorney, Agent, or Firm* — SOLARIS Intellectual Property Group, PLLC

(57) ABSTRACT

A blazed diffractive optical element includes: a blazed diffraction grating pair that includes a first blazed member and a second blazed member and functions as a diffraction grating with the first blazed member and the second blazed member; and an interlayer that is positioned between the first blazed member and the second blazed member, in which in a case where a refractive index of the first blazed member is represented by Na, a refractive index of the interlayer is represented by N, and a refractive index of the second blazed member is represented by Nb, a magnitude relationship of Na>N>Nb is satisfied.

16 Claims, 18 Drawing Sheets

(58) Field of Classification Search
CPC .............. A61F 2250/0026; A61F 2/16; B29D
11/0026; B29D 11/00884; B29D 11/023;
G02C 7/06
See application file for complete search history.

(56) References Cited

U.S. PATENT DOCUMENTS

| | | | | |
|---|---|---|---|---|
| 2006/0050234 | A1* | 3/2006 | Morris .................. | A61F 2/1613 |
| | | | | 623/6.3 |
| 2009/0141354 | A1 | 6/2009 | Kobayashi | |
| 2011/0122305 | A1* | 5/2011 | Kobayashi ......... | G02B 27/0037 |
| | | | | 359/566 |
| 2017/0216019 | A1* | 8/2017 | Shimizu .................. | A61F 2/161 |
| 2018/0132996 | A1 | 5/2018 | Tiwari et al. | |
| 2019/0041664 | A1 | 2/2019 | Ando | |

FOREIGN PATENT DOCUMENTS

| | | |
|---|---|---|
| JP | 2009-134223 A | 6/2009 |
| JP | 2011-107586 A | 6/2011 |
| JP | 2018-189863 A | 11/2018 |
| JP | 2019066756 A * | 4/2019 |
| JP | 2019-534071 A | 11/2019 |
| WO | 2017/138099 A1 | 8/2018 |

OTHER PUBLICATIONS

Written Opinion of the ISA issued in International Application No. PCT/JP2021/021755 on Aug. 31, 2021.
English language translation of the following: Office action dated Jan. 30, 2024 from the JPO in a Japanese patent application No. 2022-533786 corresponding to the instant patent application.
English language translation of the following: Notice dated Jul. 16, 2025 from the SIPO in a Chinese patent application No. 202180042935.4 corresponding to the instant patent application. This office action translation is submitted now in order to supplement the understanding of the cited references which are being disclosed in the instant Information Disclosure Statement.

* cited by examiner

[ASPECT OBSERVED FROM LOWER SIDE IN Z DIRECTION]

[ASPECT OBSERVED FROM UPPER SIDE IN Z DIRECTION]

【FIRST BLAZED MEMBER FORMING STEP】

【FIRST BLAZED MEMBER FORMING STEP】

【FIRST BLAZED MEMBER FORMING STEP】

【INTERLAYER FORMING STEP】

[INTERLAYER FORMING STEP]

【SECOND BLAZED MEMBER FORMING STEP】

【SECOND BLAZED MEMBER FORMING STEP】

[SECOND BLAZED MEMBER FORMING STEP]

102A (EXAMPLE: REFRACTIVE INDEX = 1.58)

102

106B

106A 108B 108A

106

108

104

104A (EXAMPLE: REFRACTIVE INDEX = 1.56)

100

100

$\theta 1$ (EXAMPLE: 5°)   $\theta 1$ (EXAMPLE: 5°)

102

SUBJECT LIGHT (EXAMPLE: REFRACTIVE INDEX = 1.58)

STEEP SLOPE SURFACE

STEEP SLOPE SURFACE

104

GENTLE SLOPE SURFACE $\theta 2$ (EXAMPLE: 7°)   $\theta 2$ (EXAMPLE: 7°)

(EXAMPLE: REFRACTIVE INDEX = 1.56)

(CAPTURED IMAGE)

GHOSTING CAUSED BY REFRACTION

LIGHT SOURCE IMAGE

FIG. 17

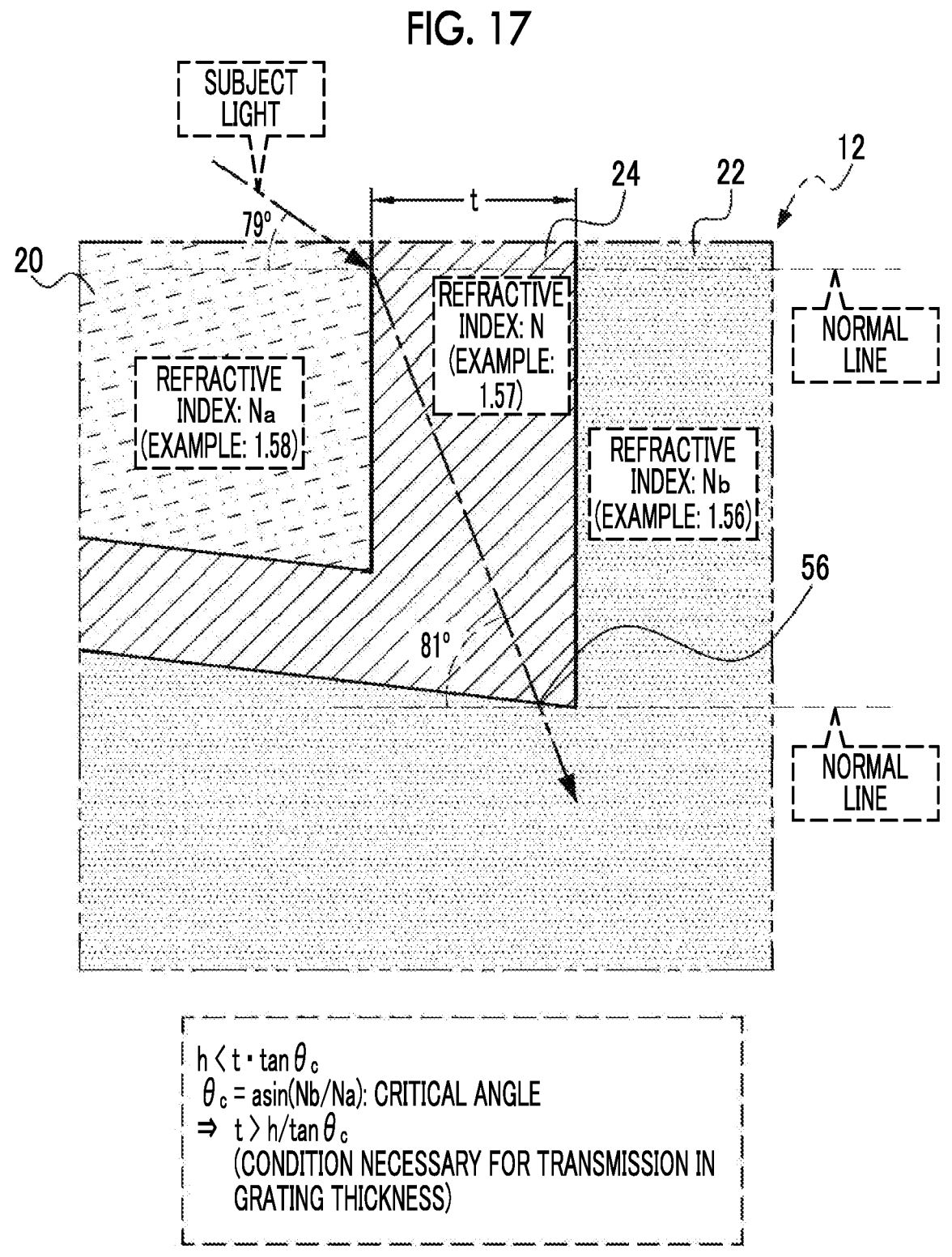

SUBJECT
LIGHT

79°

20

REFRACTIVE
INDEX: Na
(EXAMPLE: 1.58)

t

24

22

12

REFRACTIVE
INDEX: N
(EXAMPLE:
1.57)

NORMAL
LINE

REFRACTIVE
INDEX: Nb
(EXAMPLE: 1.56)

56

81°

NORMAL
LINE $h < t \cdot \tan \theta_c$ $\theta_c = \mathrm{asin}(Nb/Na)$: CRITICAL ANGLE $\Rightarrow \ t > h/\tan \theta_c$ (CONDITION NECESSARY FOR TRANSMISSION IN GRATING THICKNESS)

BLAZED DIFFRACTIVE OPTICAL ELEMENT AND METHOD OF MANUFACTURING BLAZED DIFFRACTIVE OPTICAL ELEMENT

CROSS-REFERENCE TO RELATED APPLICATIONS

This application is a continuation application of International Application No. PCT/JP2021/021755, filed on Jun. 8, 2021, the disclosure of which is incorporated herein by reference in its entirety. Further, this application claims priority from Japanese Patent Application No. 2020-113523, filed on Jun. 30, 2020, the disclosure of which is incorporated herein by reference in its entirety.

BACKGROUND

1. Technical Field

The disclosed technology discloses a blazed diffractive optical element and a method of manufacturing a blazed diffractive optical element.

2. Related Art

JP2011-107586A discloses a diffractive optical element where a plurality of diffraction gratings consisting of at least three materials are laminated. In the diffractive optical element described in JP2011-107586A, the plurality of diffraction gratings includes: a first combination part including two diffraction gratings made of materials M1A and M1B different from each other in which grating side surfaces of grating parts contact with each other or are disposed close to each other in a grating pitch direction; and a second combination part including two diffraction gratings made of materials M2A and M2B different from each other in which at least one material is different from the materials of the two diffraction gratings of the first combination part. The values of refractive indices N1Aw and N1Bw of the materials M1A and M1B forming the first combination part at a wavelength (w) (nm), Abbe numbers v1A and v1B of the materials M1A and M1B, refractive indices N2Ad and N2Bd of the materials M2A and M2B forming the second combination part on a d-line, and Abbe numbers v2A and v2B of the materials M2A and M2B are appropriately set.

SUMMARY

One embodiment of the disclosed technology provides: a blazed diffractive optical element that can suppress ghosting caused by incident light as compared to a case where a first blazed member and a second blazed member are directly laminated; and a method of manufacturing a blazed diffractive optical element.

In a first aspect of the disclosed technology, there is provided a blazed diffractive optical element comprising: a blazed diffraction grating pair that includes a first blazed member and a second blazed member and functions as a diffraction grating with the first blazed member and the second blazed member; and an interlayer that is positioned between the first blazed member and the second blazed member, in which in a case where a refractive index of the first blazed member is represented by Na, a refractive index of the interlayer is represented by N, and a refractive index of the second blazed member is represented by Nb, a magnitude relationship of Na>N>Nb is satisfied.

According to a second aspect of the disclosed technology, in the blazed diffractive optical element according to the first aspect, in a case where a grating height of the first blazed member and the second blazed member is represented by h, a thickness of the interlayer is represented by t, and in a case where a critical angle is represented by θc, an inequality of h<t·tan θc and an equality of θc=a sin(Nb/Na) are satisfied.

According to a third aspect of the disclosed technology, in the blazed diffractive optical element according to the first aspect or the second aspect, the first blazed member has a first serrated surface, the second blazed member has a second serrated surface, and the first serrated surface and the second serrated surface complementarily engage with each other through the interlayer.

According to a fourth aspect of the disclosed technology, in the blazed diffractive optical element according to the first aspect or the second aspect, the first blazed member has a first serrated surface, the second blazed member has a second serrated surface, the first serrated surface is formed with a first steep slope surface and a first gentle slope surface having a gentler gradient than the first steep slope surface, the second serrated surface is formed of a second steep slope surface and a second gentle slope surface having a gentler gradient than the second steep slope surface, and the interlayer is disposed between the first steep slope surface and the second steep slope surface in a position between the first serrated surface and the second serrated surface.

According to a fifth aspect of the disclosed technology, in the blazed diffractive optical element according to the third aspect, the first serrated surface is formed with a first steep slope surface and a first gentle slope surface having a gentler gradient than the first steep slope surface, the second serrated surface is formed of a second steep slope surface and a second gentle slope surface having a gentler gradient than the second steep slope surface, and the interlayer is disposed between the first steep slope surface and the second steep slope surface in a position between the first serrated surface and the second serrated surface.

According to a sixth aspect of the disclosed technology, in the blazed diffractive optical element according to the first aspect, the first blazed member has a first serrated surface, the second blazed member has a second serrated surface, the first serrated surface is formed with a first steep slope surface and a first gentle slope surface having a gentler gradient than the first steep slope surface, the second serrated surface is formed of a second steep slope surface and a second gentle slope surface having a gentler gradient than the second steep slope surface, and in a case where a thickness of the interlayer that is disposed between the first steep slope surface and the second steep slope surface in a position between the first serrated surface and the second serrated surface is represented by t, a grating height of the first blazed member and the second blazed member is represented by h, and a critical angle is represented by θc, an inequality of h<t·tan θc and an equality of θc=a sin(Nb/Na) are satisfied.

According to a seventh aspect of the disclosed technology, in the blazed diffractive optical element according to any one of the fourth aspect to the sixth aspect, the first blazed member has a first reference surface, the second blazed member has a second reference surface, the first steep slope surface and the first gentle slope surface are surfaces that rise from the first reference surface, the second steep slope surface and the second gentle slope surface are surfaces that rise from the second reference surface, the first steep slope surface is perpendicular to the first reference surface, and the second steep slope surface is perpendicular to the second reference surface.

According to an eighth aspect of the disclosed technology, in the blazed diffractive optical element according to any one of the third aspect to the seventh aspect, the first serrated surface and the second serrated surface are shifted from each other by a thickness of the interlayer and are engaged with each other.

According to a ninth aspect of the disclosed technology, in the blazed diffractive optical element according to any one of the first aspect to the eighth aspect, the interlayer consists of a plurality of layers where a refractive index decreases from the first blazed member side to the second blazed member side.

According to a tenth aspect of the disclosed technology, in the blazed diffractive optical element according to any one of the first aspect to the ninth aspect, the interlayer is formed in a film.

According to an eleventh aspect of the disclosed technology, in the blazed diffractive optical element according to any one of the first aspect to the tenth aspect, a blaze angle of the first blazed member and a blaze angle of the second blazed member are the same.

According to a twelfth aspect of the disclosed technology, in the blazed diffractive optical element according to any one of the first aspect to the eleventh aspect, a grating height of the first blazed member and a grating height of the second blazed member are the same.

According to a thirteenth aspect of the disclosed technology, there is provided a blazed diffractive optical element comprising: a blazed member; and a layer that is provided on the blazed member, in which a refractive index of the layer is between a refractive index of the blazed member and a refractive index of an ambient environment around the blazed member.

According to a fourteenth aspect of the disclosed technology, in the blazed diffractive optical element according to the thirteenth aspect, the ambient environment is anterior chamber aqueous humor in an eye, and the refractive index of the layer is between the refractive index of the blazed member and a refractive index of the anterior chamber aqueous humor.

According to a fifteenth aspect of the disclosed technology, in the blazed diffractive optical element according to the fourteenth aspect, in a case where the refractive index of the anterior chamber aqueous humor is represented by A, the refractive index of the surface layer is represented by B, and the refractive index of the blazed member is represented by C, a magnitude relationship of $A<B<C$ is satisfied.

According to a sixteenth aspect of the disclosed technology, in the blazed diffractive optical element according to the fifteenth aspect, in a case where a grating height of the blazed member is represented by h, a thickness of the layer is represented by t, and a critical angle is represented by $\theta c$, an inequality of $h<t \cdot \tan \theta c$ and an equality of $\theta c = a \sin(A/C)$ are satisfied.

According to a seventeenth aspect of the disclosed technology, in the blazed diffractive optical element according to the fifteenth aspect or the sixteenth aspect, the blazed member has a serrated surface, and the layer is formed on the serrated surface in a shape corresponding to the serrated surface.

According to an eighteenth aspect of the disclosed technology, in the blazed diffractive optical element according to the seventeenth aspect, the serrated surface is formed with a steep slope surface and a gentle slope surface having a gentler gradient than the steep slope surface.

According to a nineteenth aspect of the disclosed technology, in the blazed diffractive optical element according to the eighteenth aspect, the blazed member has a reference surface, the steep slope surface and the gentle slope surface are surfaces that rise from the reference surface, and the steep slope surface is perpendicular to the reference surface.

According to a twentieth aspect of the disclosed technology, in the blazed diffractive optical element according to any one of the seventeenth aspect to the nineteenth aspect, the serrated surface and the anterior chamber aqueous humor are offset from each other by a thickness of the layer and are in contact with each other.

According to a twenty first aspect of the disclosed technology, in the blazed diffractive optical element according to any one of the fourteenth aspect to the twentieth aspect, the surface layer consists of a plurality of layers where a refractive index increases from the anterior chamber aqueous humor side to the blazed member side.

According to a twenty second aspect of the disclosed technology, in the blazed diffractive optical element according to any one of the thirteenth aspect to the twenty first aspect, the surface layer is formed in a film shape.

According to a twenty third aspect of the disclosed technology, there is provided a method of manufacturing a blazed diffractive optical element, the method comprising: a step of forming a first blazed member; a step of forming an interlayer on a blazed portion of the first blazed member; and a step of forming a second blazed member that is provided on a side of the interlayer opposite to the first blazed member side and forms a pair with the first blazed member, in which in a case where a refractive index of the first blazed member is represented by Na, a refractive index of the interlayer is represented by N, and a refractive index of the second blazed member is represented by Nb, a magnitude relationship of $Na>N>Nb$ is satisfied.

According to a twenty fourth aspect of the disclosed technology, in the method of manufacturing a blazed diffractive optical element according to the twenty third aspect, the step of forming the interlayer is a step of forming the interlayer by spin coating.

According to a twenty fifth aspect of the disclosed technology, in the method of manufacturing a blazed diffractive optical element according to the twenty third aspect or the twenty fourth aspect, in a case where a grating height of the first blazed member and the second blazed member is represented by h, a thickness of the interlayer is represented by t, and a critical angle is represented by $\theta c$, the interlayer having a thickness that satisfies an inequality of $h>t \cdot \tan \theta c$ and an equality of $\theta c = a \sin(Nb/Na)$ is formed.

According to a twenty sixth aspect of the disclosed technology, in the method of manufacturing a blazed diffractive optical element according to the twenty third aspect or the twenty fifth aspect, the first blazed member has a first serrated surface, the second blazed member has a second serrated surface, and in the step of forming the second blazed member, the first serrated surface and the second serrated surface are shifted from each other by a thickness of the interlayer and are engaged with each other.

BRIEF DESCRIPTION OF THE DRAWINGS

Exemplary embodiments of the technology of the disclosure will be described in detail based on the following figures, wherein:

FIG. 17 is a schematic partial cross-sectional view showing an example of an aspect of the inside of the laminated blazed diffractive optical element in a case where subject light is incident into the laminated blazed diffractive optical element;

DETAILED DESCRIPTION

Hereinafter, an example of an embodiment of a laminated blazed diffractive optical element and a method of manufacturing a laminated blazed diffractive optical element according to the disclosed technology will be described with reference to the accompanying drawings.

In the description of the present specification, "perpendicular" refers to not only being completely perpendicular but also being perpendicular with the meaning encompassing error that is generally allowable in the technical field to which the disclosed technology belongs within a range not departing from the scope of the disclosed technology. In addition, in the description of the present specification, "orthogonal" refers to not only being completely orthogonal but also being orthogonal with the meaning encompassing error that is generally allowable in the technical field to which the disclosed technology belongs within a range not departing from the scope of the disclosed technology. In addition, in the description of the present specification, "parallel" refers to not only being completely parallel but also being parallel with the meaning encompassing error that is generally allowable in the technical field to which the disclosed technology belongs within a range not departing from the scope of the disclosed technology. In addition, in the description of the present specification, "the same" refers to not only being completely the same but also being the same with the meaning encompassing error that is generally allowable in the technical field to which the disclosed technology belongs within a range not departing from the scope of the disclosed technology.

<Overall Configuration of Bonded Optical Element>

Figure 1:
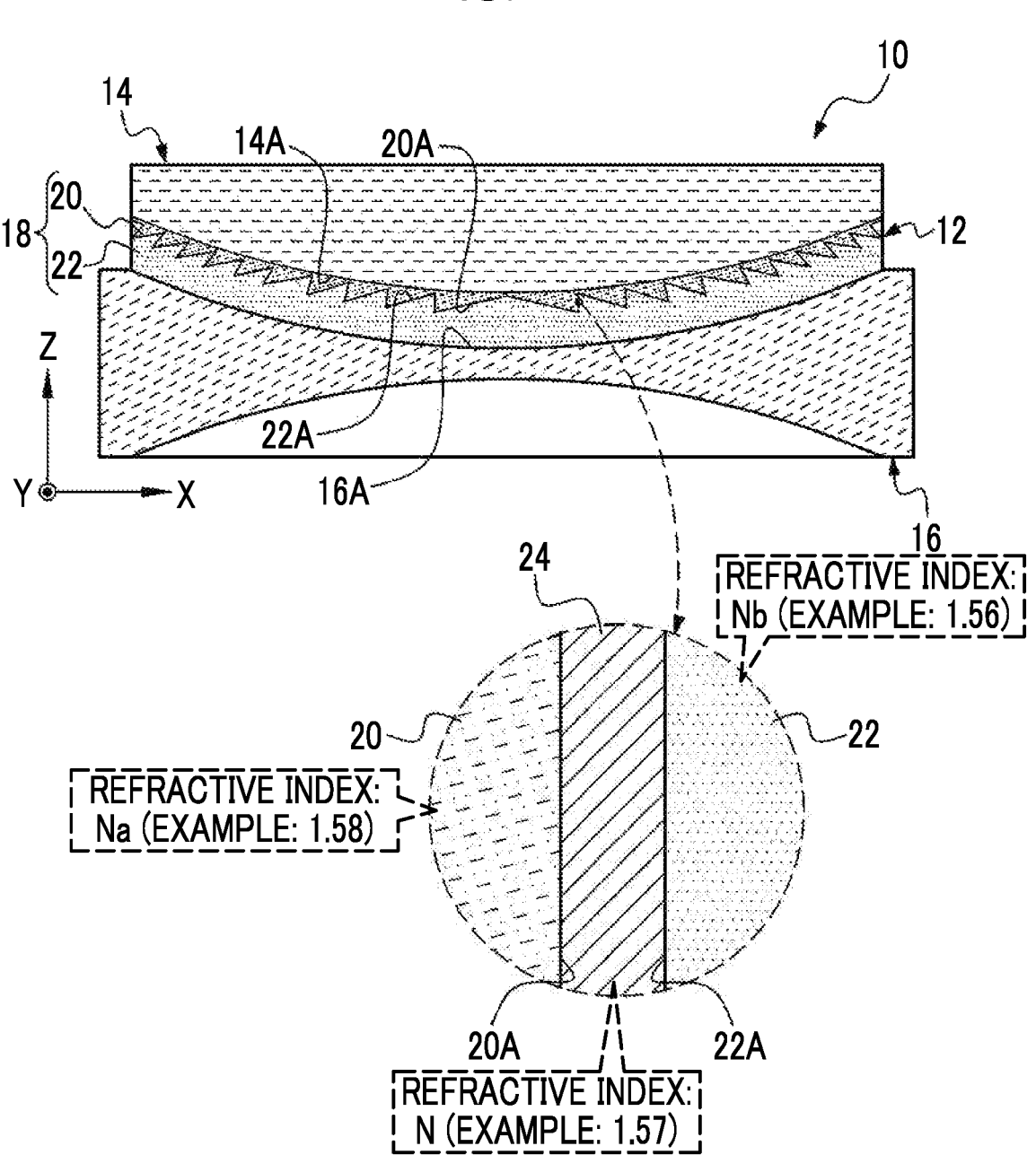
FIG. 1 is a schematic cross-sectional view showing an example of a cross-sectional structure of a bonded optical element.

For example, as shown in FIG. 1, a bonded optical element 10 includes a pair of lenses and a laminated blazed diffractive optical element 12. The bonded optical element 10 is used as, for example, a lens of an optical device (for example, a digital camera, a projector, or a microscope) or a lens of a vision correction tool (for example, glasses or contact lenses).

Figure 2:
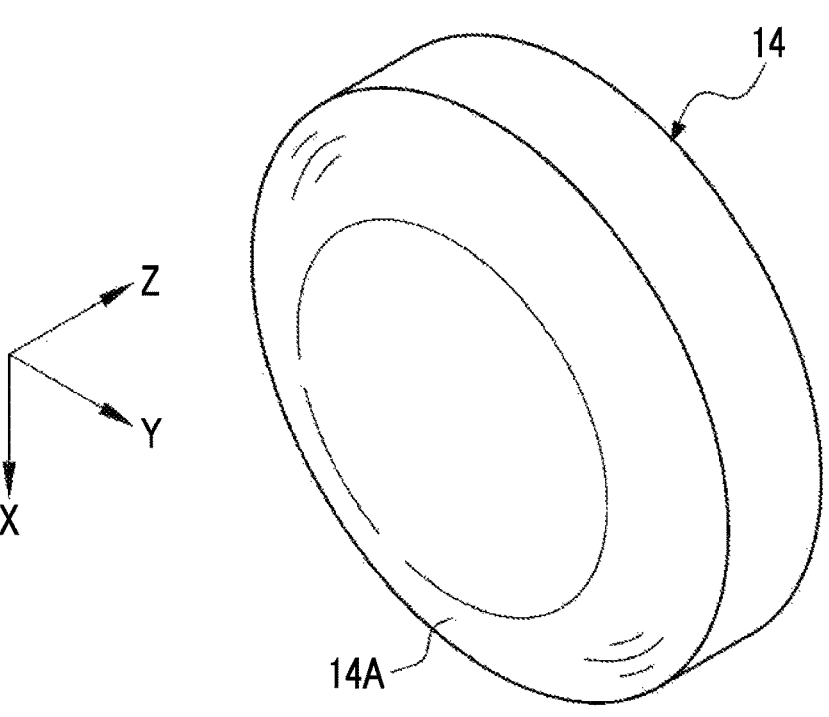
FIG. 2 is a schematic perspective view showing an example of the external appearance of a plano-convex lens used in the bonded optical element.
Figure 3:
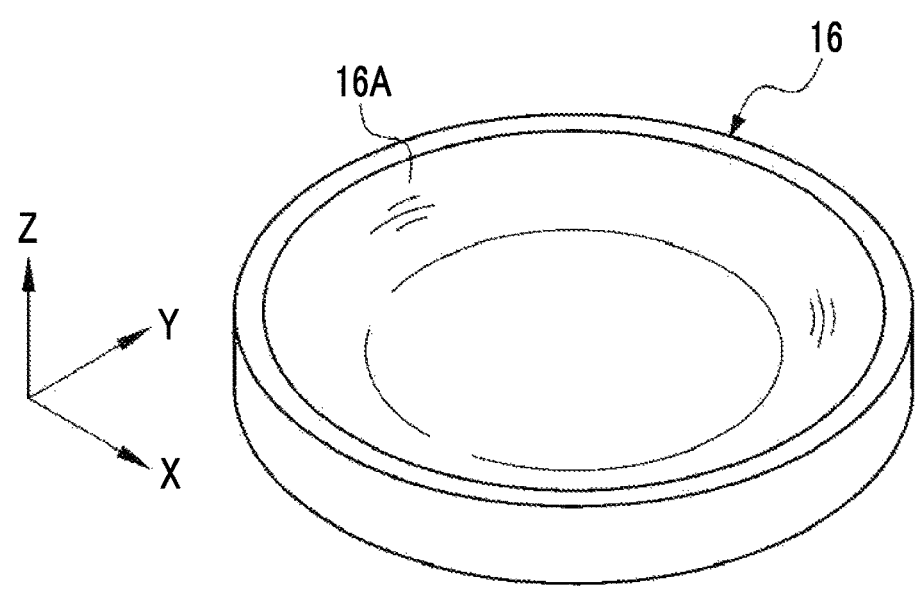
FIG. 3 is a schematic perspective view showing an example of the external appearance of a biconcave lens used in the bonded optical element.
Figure 8:
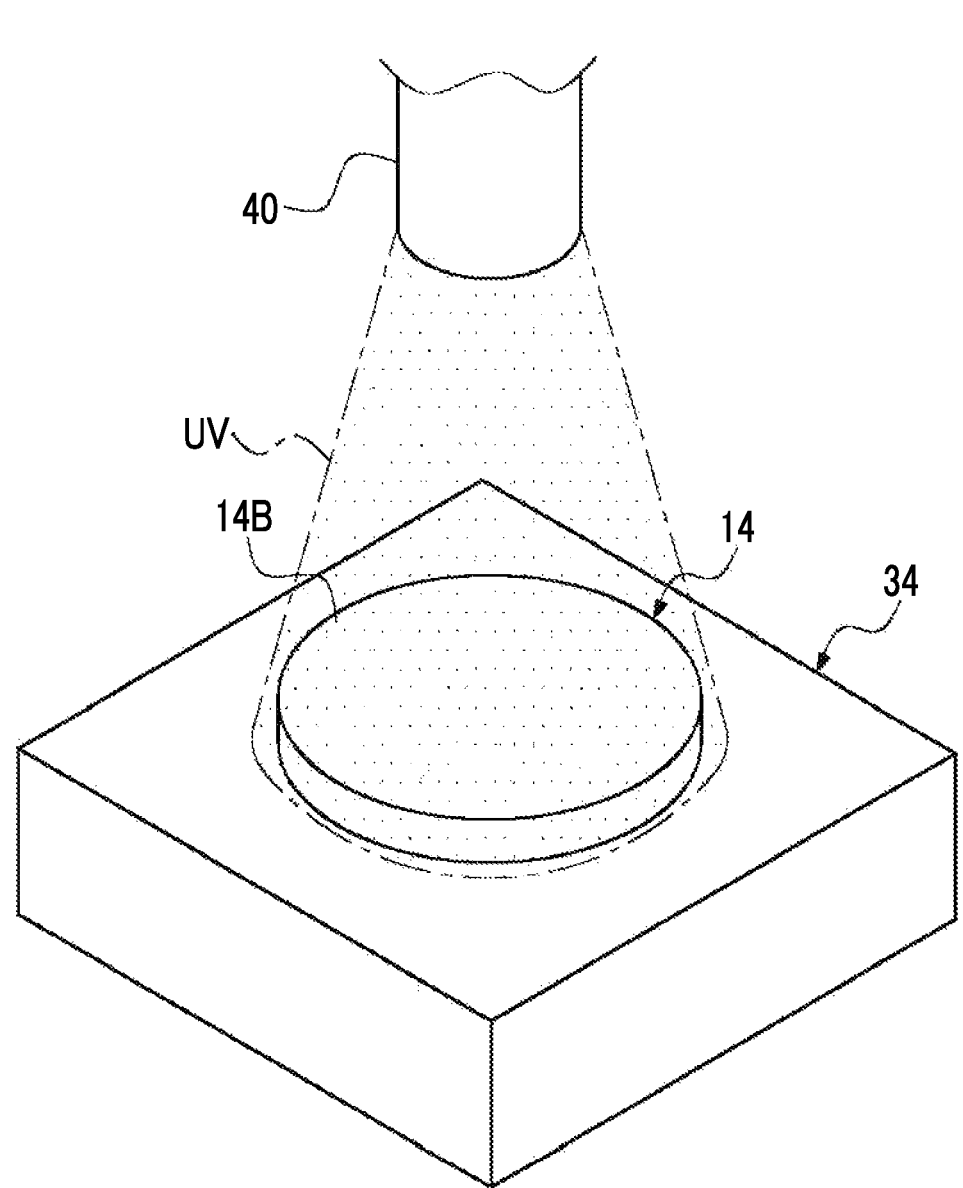
FIG. 8 is a schematic perspective view showing an example of an aspect where ultraviolet light is emitted from a plane side of the plano-convex lens in the first blazed member forming step.
Figure 10:
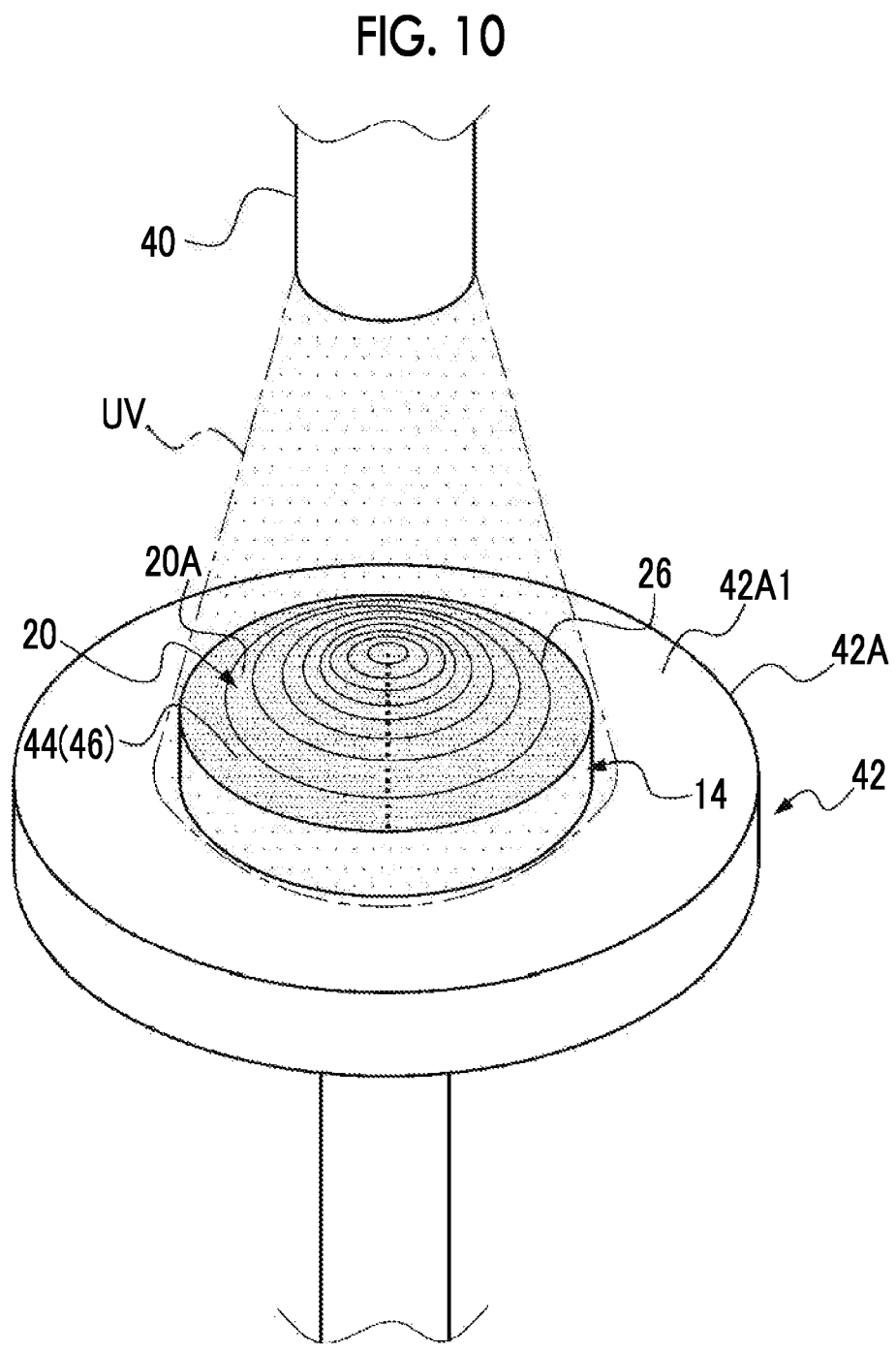
FIG. 10 is a schematic perspective view showing an example of an aspect where the ultraviolet curable resin applied to the entire surface of the first blazed member is irradiated with ultraviolet light in the interlayer forming step.
Figure 13:
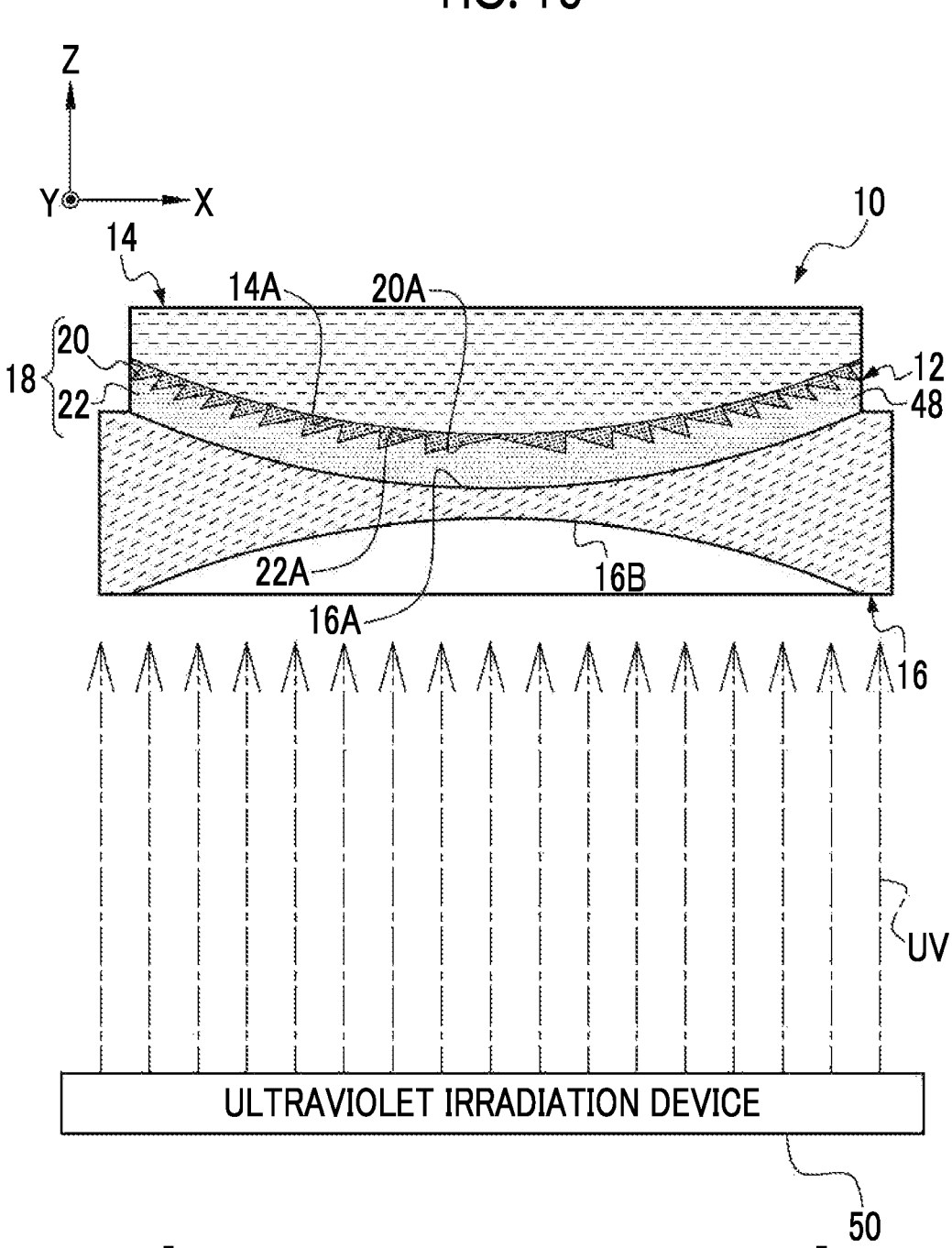
FIG. 13 is a conceptual diagram showing an example of an aspect where ultraviolet light is emitted from another concave surface side of the biconcave lens in the second blazed member forming step.

The pair of lenses in the bonded optical element 10 are lenses made of glass and allow transmission of ultraviolet light UV (refer to FIGS. 8, 10, and 13). In the example shown in FIG. 1, as the pair of lenses, a plano-convex lens 14 (refer to FIG. 2) and a biconcave lens 16 (refer to FIG. 3) are shown. Here, as the pair of lenses, a combination of the plano-convex lens 14 and the biconcave lens 16 is shown. However, this configuration is merely exemplary, and The pair of lenses may be another combination of lenses (a combination of a biconvex lens and a plano-concave lens). In addition, the pair of lenses do not need to be made of glass and may be made of a resin.

Hereinafter, for convenience of description, it is assumed that a thickness direction of the plano-convex lens 14 and the biconcave lens 16 is a Z direction, a width direction of the plano-convex lens 14 and the biconcave lens 16 is an X direction, and a depth direction of the plano-convex lens 14 and the biconcave lens 16, that is, a direction orthogonal to the Z direction and the X direction is a Y direction.

The laminated blazed diffractive optical element 12 is an example of "the blazed diffractive optical element" according to the disclosed technology and includes a blazed diffraction grating pair 18. The blazed diffraction grating pair 18 includes a first blazed member 20 and a second blazed member 22, and functions as a diffraction grating with the first blazed member 20 and the second blazed member 22.

Figure 4:
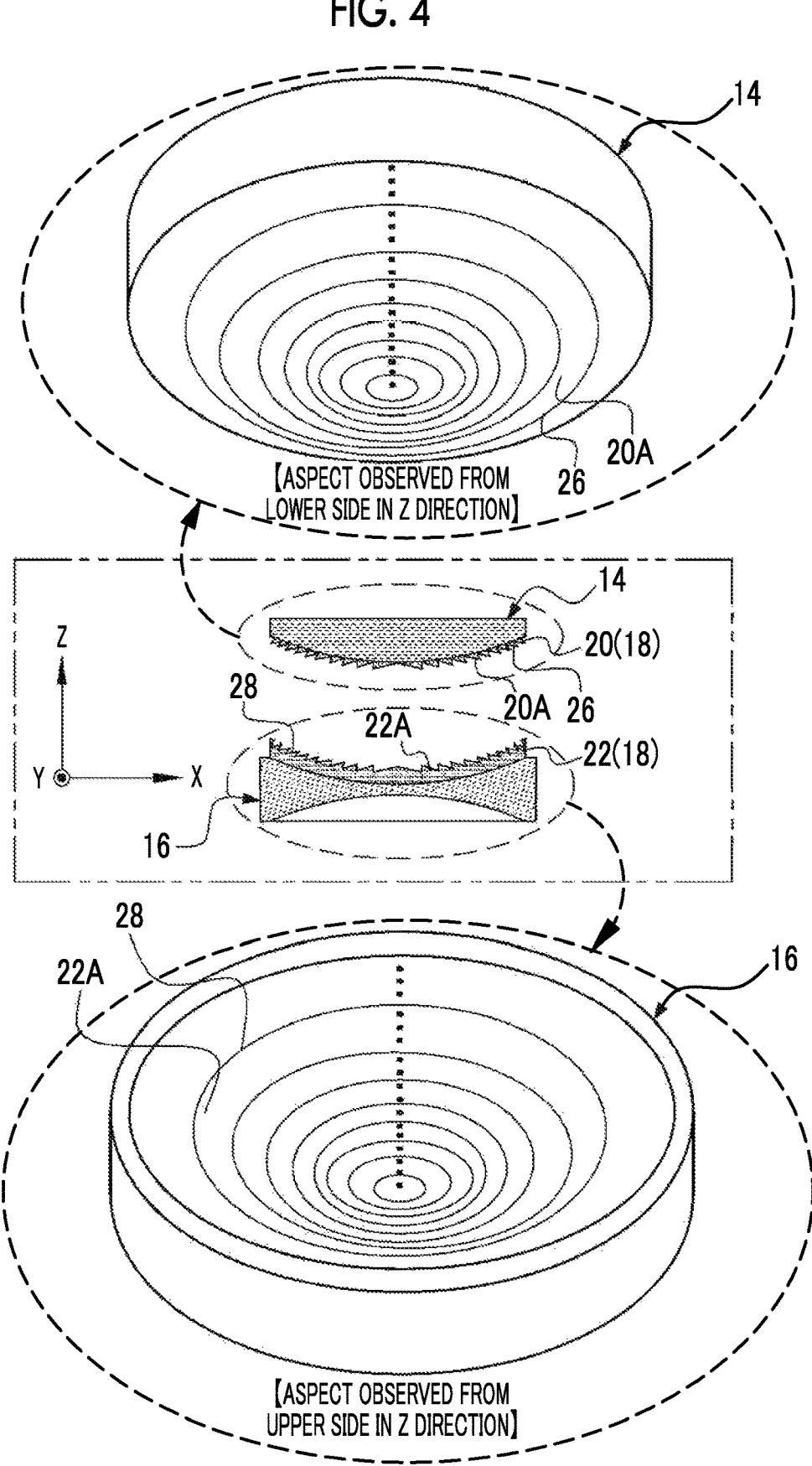
FIG. 4 is a conceptual diagram showing an example of the external appearances of a first serrated surface and a second serrated surface.

For example, as shown in FIG. 1, the first blazed member 20 has a front surface and a back surface in the Z direction, and the back surface is bonded to a convex surface 14A (refer to FIG. 2) of the plano-convex lens 14. The front surface of the first blazed member 20 is a first serrated surface 20A. The first serrated surface 20A is formed in a serrated shape in cross-section. For example, as shown in FIG. 4, in a case where the first blazed member 20 is observed from the lower side in the Z direction, a wedge-shaped groove 26 is concentrically formed in the first serrated surface 20A.

For example, as shown in FIG. 1, the second blazed member 22 has a front surface and a back surface in the Z direction, and the back surface is bonded to one concave surface 16A (refer to FIG. 3) of the biconcave lens 16. The front surface of the second blazed member 22 is a second serrated surface 22A. The second serrated surface 22A is formed in a serrated shape in cross-section. For example, as shown in FIG. 4, in a case where the second blazed member 22 is observed from the lower side in the Z direction, a wedge-shaped groove 28 is concentrically formed in the second serrated surface 22A.

For example, as shown in FIG. 1, the laminated blazed diffractive optical element 12 includes an interlayer 24. The interlayer 24 is positioned between the first blazed member 20 and the second blazed member 22.

Here, in a case where a refractive index of the first blazed member 20 is represented by Na, a refractive index of the interlayer 24 is represented by N, and a refractive index of the second blazed member 22 is represented by Nb, a magnitude relationship of "Na>N>Nb" is satisfied. In the example shown in FIG. 1, "1.58" is shown as an example of the refractive index Na, "1.57" is shown as an example of the refractive index N, and "1.56" is shown as an example of the refractive index Nb.

<Method of Manufacturing Laminated Blazed Diffractive Optical Element>

Figure 5:
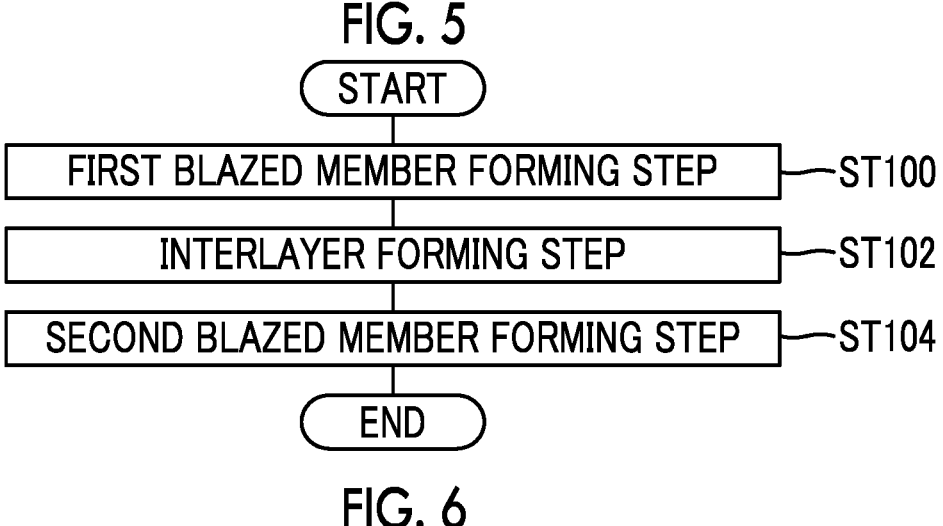
FIG. 5 is a flowchart showing an example of a method of manufacturing a laminated blazed diffractive optical element.

FIG. 5 shows an example of the method of manufacturing the laminated blazed diffractive optical element 12. The manufacturing method shown in FIG. 5 includes a first blazed member forming step of Step ST100, an interlayer forming step of Step ST102, and a second blazed member forming step of Step ST104.

In Step ST100, the first blazed member 20 is formed. In Step ST102, the interlayer 24 is formed on the first serrated surface 20A of the first blazed member 20. The first serrated surface 20A is an example of "the blazed portion" according to the disclosed technology. In Step ST104, the second blazed member 22 that forms a pair with the first blazed member 20 is formed on a side of the interlayer 24 opposite to the first blazed member 20 side. The first blazed member forming step, the interlayer forming step, and the second blazed member forming step will be described in more detail.

<First Blazed Member Forming Step>

Figure 6:
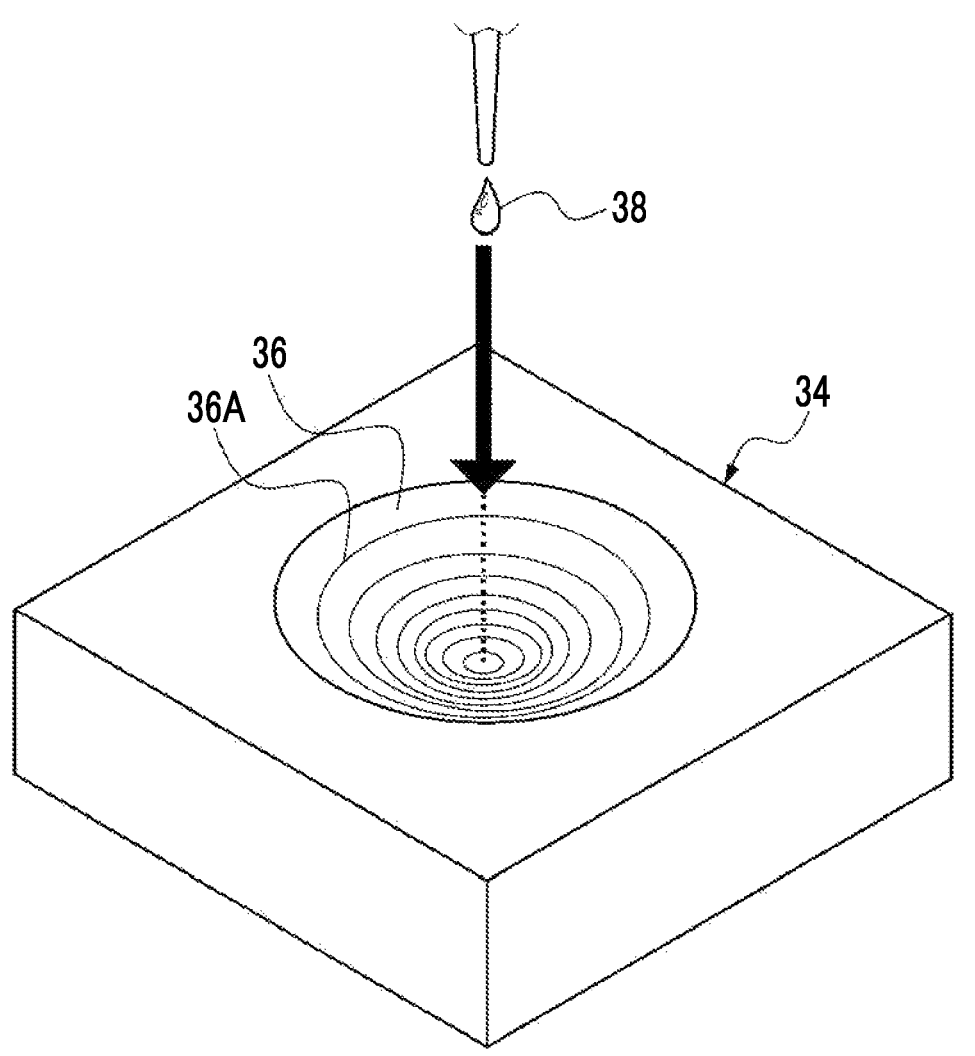
FIG. 6 is a schematic perspective view showing an example of an aspect where an ultraviolet curable resin is cast into a cavity in a first blazed member forming step.

In a case where the first blazed member 20 is prepared, for example, a cavity 34 is used as shown in FIG. 6. The cavity 34 is a mold for molding the first serrated surface 20A. A depression 36 is formed in a center portion of the cavity 34. The depression 36 is formed in a bowl shape. A surface of the depression 36 is a concentric surface 36A. The concentric surface 36A is a surface where a wedge-shaped groove (for example, a groove corresponding to the wedge-shaped groove shown in FIG. 4) is concentrically formed around the center of the bottom of the depression 36. The size and the shape of the concentric surface 36A corresponds to the second serrated surface 22A. That is, the concentric surface 36A is formed with the same size and shape as those of second serrated surface 22A.

A liquid ultraviolet curable resin 38 for the first blazed member 20 is cast into the depression 36 to prevent entrance of bubbles. The size and the shape of the concentric surface 36A are designed in consideration of a shrinkage ratio of the ultraviolet curable resin 38 in a case where the ultraviolet curable resin 38 in the depression 36 is irradiated with the ultraviolet light UV (refer to FIG. 8) in the subsequent step.

Figure 7:
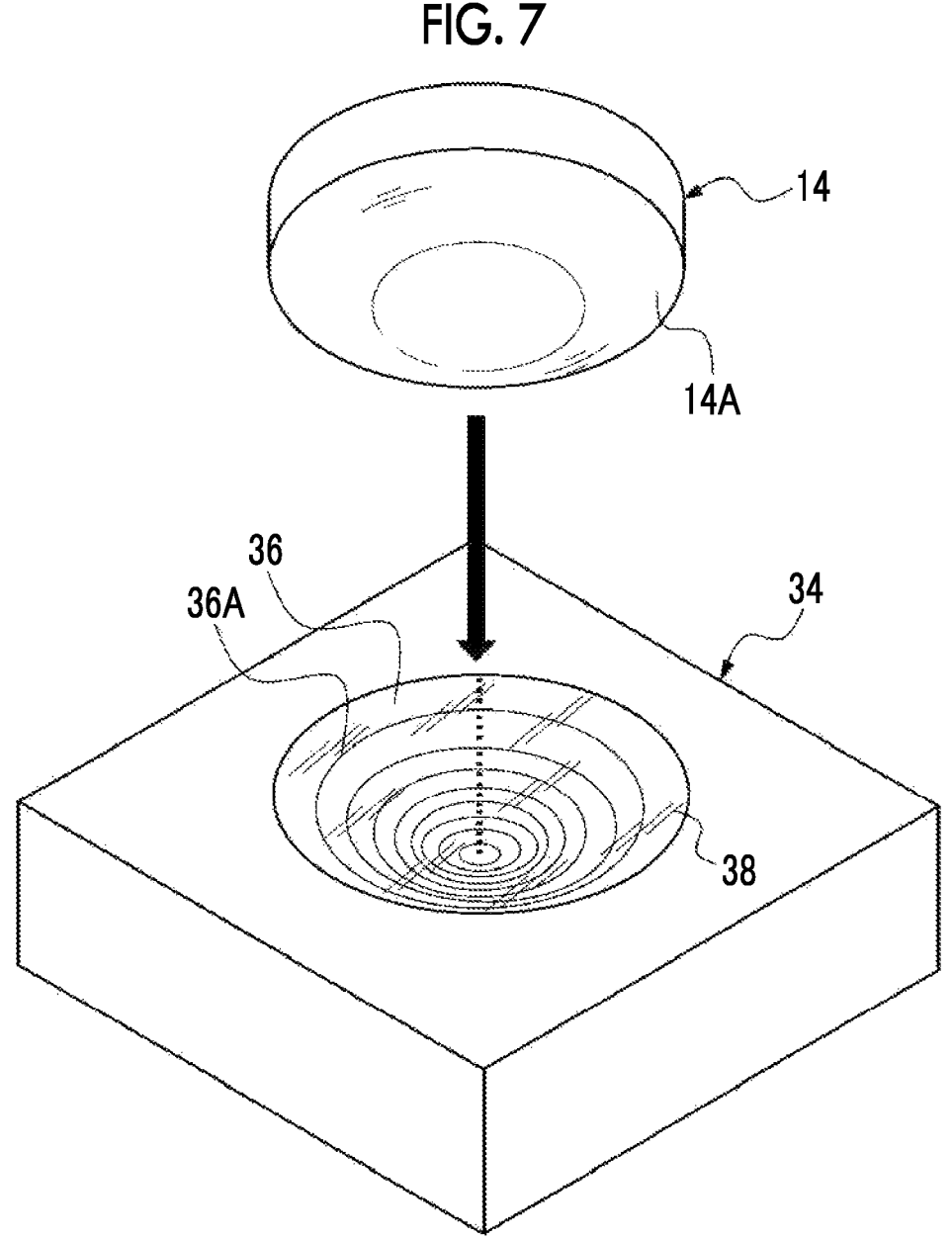
FIG. 7 is a schematic perspective view showing an example of an aspect where a convex surface of the plano-convex lens is put into the cavity into which the ultraviolet curable resin is cast in the first blazed member forming step.

In a case where the ultraviolet curable resin 38 is cast into the depression 36, the plano-convex lens 14 is subsequently put into the depression 36 such that, for example, the convex surface 14A is covered with the depression 36 as shown in FIG. 7. That is, in a state where the convex surface 14A is made to face the concentric surface 36A, the plano-convex lens 14 is buried in the ultraviolet curable resin 38 in the depression 36 from the convex surface 14A. The ultraviolet curable resin 38 that overflows from the depression 36 is wiped out.

Next, for example, as shown in FIG. 8, in a state where the plano-convex lens 14 is put into the depression 36, an ultraviolet irradiation device 40 emits the ultraviolet light UV from a plane 14B (plane opposite to the convex surface 14A) of the plano-convex lens 14. The ultraviolet light UV transmits through the plano -convex lens 14 and is emitted to the ultraviolet curable resin 38 in the depression 36. As a result, the ultraviolet curable resin 38 is cured to form the first blazed member 20 on the convex surface 14A (refer to FIGS. 1, 4, and 9).

<Interlayer Forming Step>

Figure 9:
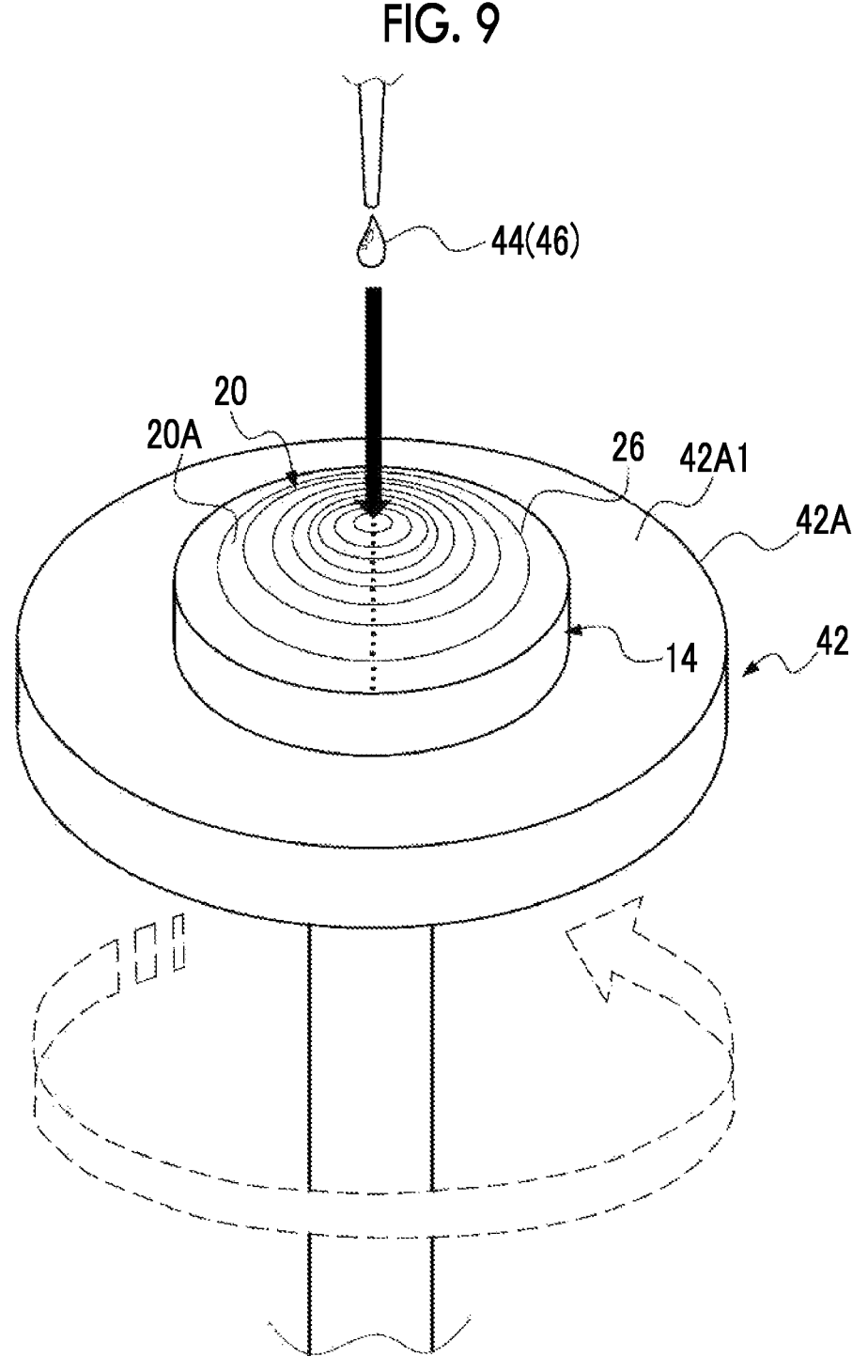
FIG. 9 is a schematic perspective view showing an example of an aspect where spin coating is performed in an interlayer forming step.

In a case where the interlayer 24 is prepared, first, the plano-convex lens 14 is taken out from the cavity 34. For example, as shown in FIG. 9, in a case where the first serrated surface 20A faces upward, the plano-convex lens 14 is provided on an upper surface 42A1 of a disk base 42A of a spin coater 42. The center of the plane 14B (refer to FIG. 8) of the plano-convex lens 14 is aligned with the center of the upper surface 42A1, and the plano-convex lens 14 is attached to the upper surface 42A1.

Examples of a method of attaching the plano-convex lens 14 to the upper surface 42A1 include an attachment method using adsorption and/or an attachment method using a pressing member.

Next, in a state where the plano-convex lens 14 is attached to the upper surface 42A1 of the disk base 42A, a liquid ultraviolet curable resin 44 for the interlayer 24 is dropped toward the center of the first serrated surface 20A. The ultraviolet curable resin 44 is preferably an acrylic or epoxy-based ultraviolet curable resin. Next, a thermosetting resin may also be adopted instead of the ultraviolet curable resin. In addition, by changing a substituent R in a meth-acrylate-based polymer, the refractive index of the interlayer 24 can also be adjusted. In addition, by adjusting a mixing ratio between plural kinds of materials, the refractive index of the interlayer 24 may be adjusted.

Next, in a state the ultraviolet curable resin 44 is fallen toward the center of the first serrated surface 20A, the disk base 42A rotates at a high speed. Due to the rotation of the disk base 42A, a centrifugal force is applied to the ultraviolet curable resin 44, and the ultraviolet curable resin 44 is diffused and applied to the entirety of the first serrated surface 20A.

Next, for example, as shown in FIG. 10, the ultraviolet irradiation device 40 irradiates the entirety of the ultraviolet curable resin 44 that is diffused and applied to the entirety of the first serrated surface 20A with the ultraviolet light UV. As a result, the ultraviolet curable resin 44 on the first serrated surface 20A is cured to form the interlayer 24 on the first serrated surface 20A. Here, the interlayer 24 is a single layer, and thus can be formed by performing the film forming step once. However, in a case where the interlayer 24 includes multiple layers, the same film forming step can be repeatedly performed a number of times corresponding to the number of layers.

<Second Blazed Member Forming Step>

Figure 11:
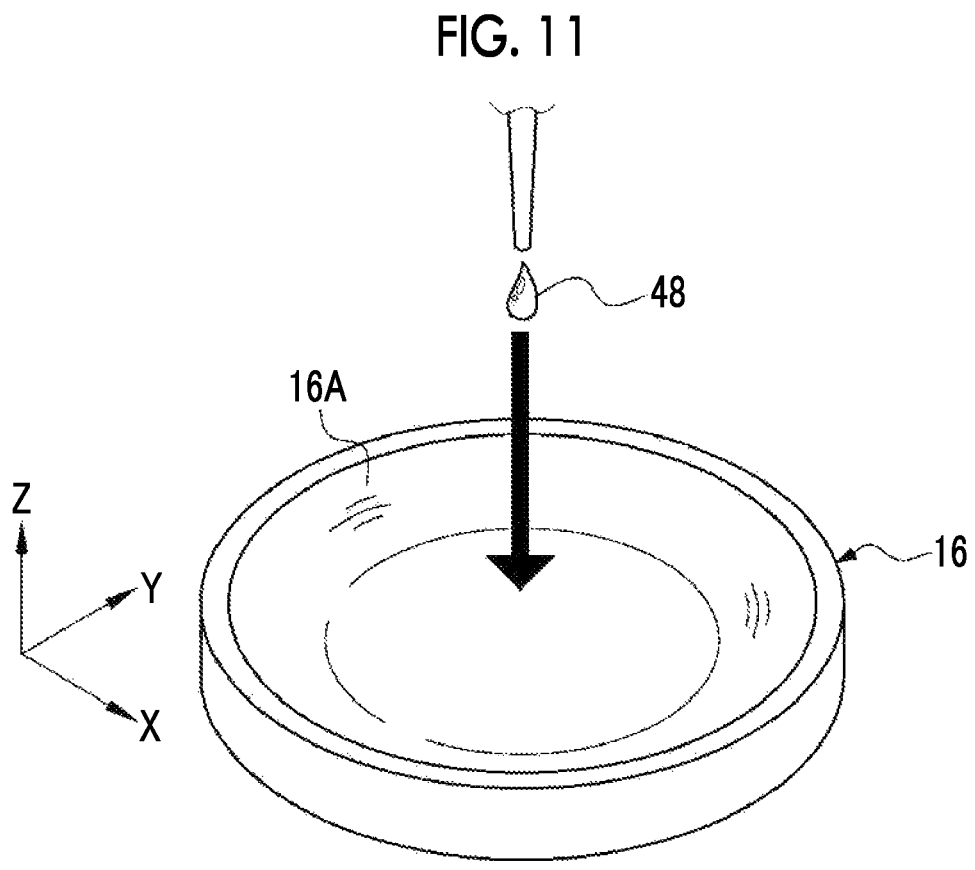
FIG. 11 is a schematic perspective view showing an example of an aspect where an ultraviolet curable resin is cast into a concave surface of the biconcave lens in a second blazed member forming step.

In a case where the second blazed member 22 is prepared, for example, as shown in FIG. 11, a liquid ultraviolet curable resin 48 for the second blazed member 22 is cast into the concave surface 16A of the biconcave lens 16 such that bubbles do not enter the concave surface 16A.

Figure 12:
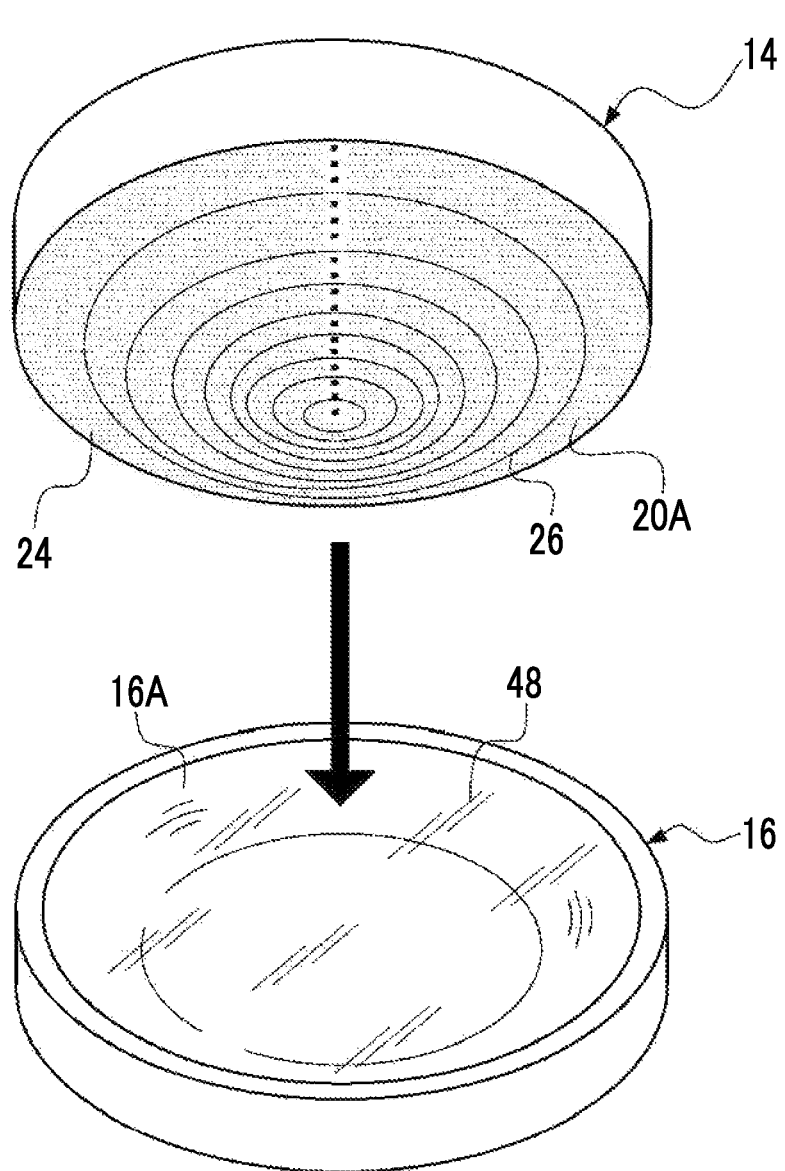
FIG. 12 is a schematic perspective view showing an example of an aspect where the plano-convex lens where an interlayer is formed on the first blazed member is put from the interlayer side into the concave surface into which the ultraviolet curable resin is cast in the second blazed member forming step.

Next, for example, as shown in FIG. 12, the plano-convex lens 14 is put into the concave surface 16A side of the biconcave lens 16 such that the interlayer 24 is covered with the concave surface 16A. That is, in a case where the interlayer 24 is made to face the concave surface 16A, the plano-convex lens 14 is buried in the ultraviolet curable resin 48 on the concave surface 16A side of the biconcave lens 16 from the interlayer 24. The ultraviolet curable resin 48 that overflows from the concave surface 16A is wiped out.

Next, for example, as shown in FIG. 13, in a state where the plano-convex lens 14 is put into the concave surface 16A side of the biconcave lens 16, an ultraviolet irradiation device 50 emits the ultraviolet light UV from another concave surface 16B (surface opposite to the concave surface 16A) of the biconcave lens 16. The ultraviolet light UV transmits through the biconcave lens 16 and is emitted to the ultraviolet curable resin 48. As a result, the ultraviolet curable resin 48 is cured to form the second blazed member 22 on the concave surface 16A.

<Laminated Blazed Diffractive Optical Element in The Related Art>

Figure 14:
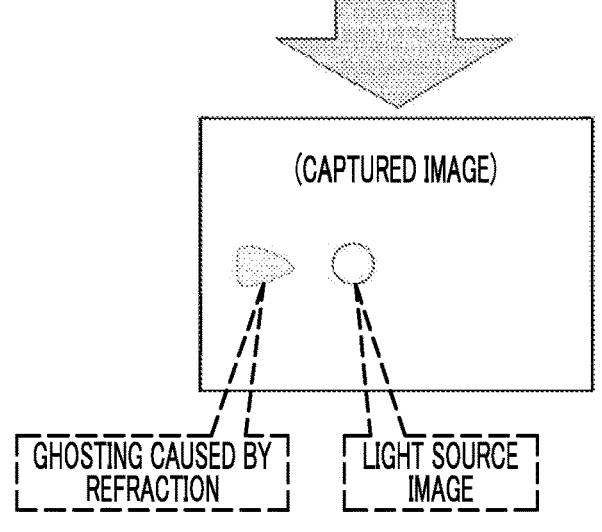
FIG. 14 is a conceptual diagram showing an example of a configuration of a laminated blazed diffractive optical element in the related art.
Figure 15:
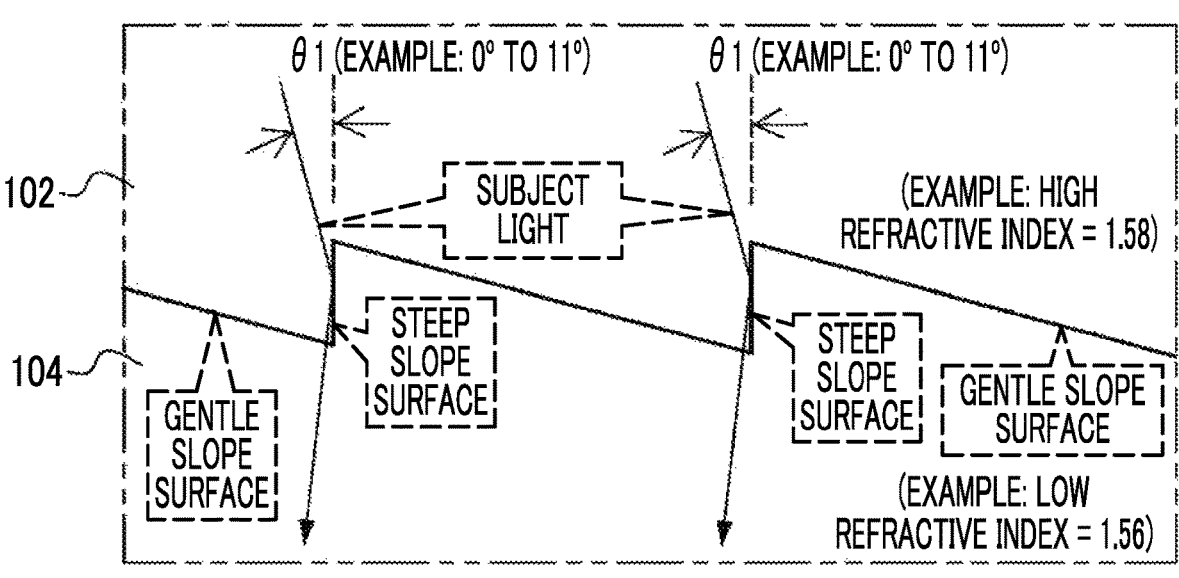
FIG. 15 is a conceptual diagram showing an example of the configuration of the laminated blazed diffractive optical element in the related art.
Figure 15:
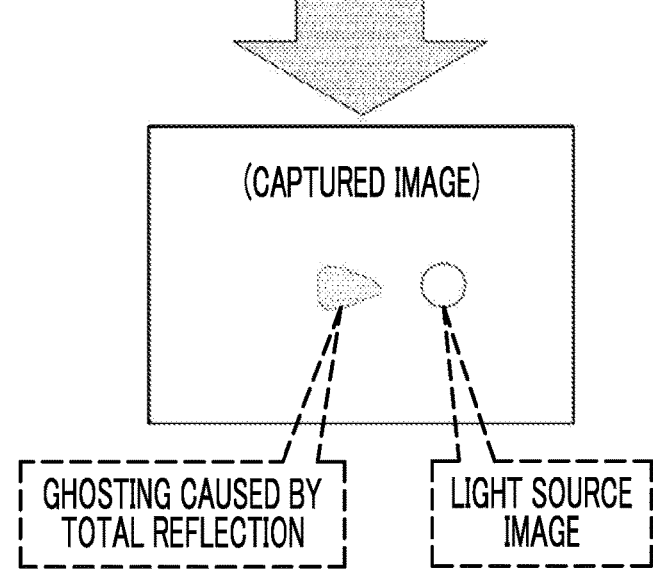
Figure 16:
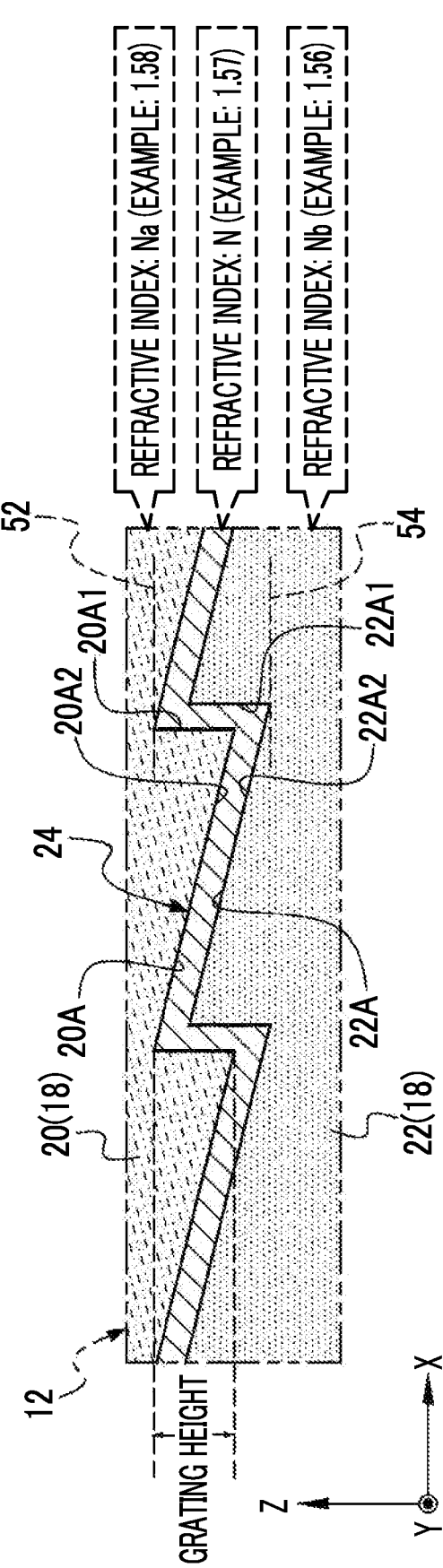
FIG. 16 is a schematic partial cross-sectional view showing an example of a configuration of a laminated blazed diffractive optical element.

As an example of a diffractive optical element in the related art, FIGS. 14 and 15 show a laminated blazed diffractive optical element not including an interlayer, that is, a laminated blazed diffractive optical element 100 where a pair of blazed members are directly engaged with each other.

For example, as shown in FIG. 14, in the laminated blazed diffractive optical element 100, a pair of blazed members are formed with a first blazed member 102 corresponding to the first blazed member 20 and a second blazed member 104 corresponding to the second blazed member 22.

The first blazed member 102 has a first serrated surface 106 corresponding to the first serrated surface 20A. The first blazed member 102 has a first reference surface 102A. The first reference surface 102A is a virtually set surface, and for example, is a surface parallel to a surface corresponding to the convex surface 14A (refer to FIG. 1).

The first serrated surface 106 is formed with a first steep slope surface 106A and a first gentle slope surface 106B. The first gentle slope surface 106B is a surface having a gentler gradient than the first steep slope surface 106A with respect to the first reference surface 102A. The first steep slope surface 106A is perpendicular to the first reference surface 102A, and the height of the first steep slope surface 106A from the first reference surface 102A is a grating height of the first blazed member 102. The first steep slope surface 106A does not need to be perpendicular to the first reference surface 102A. The reason for this is that, in an optical system used, the angle of the first steep slope surface 106A is appropriately set such that the diffraction efficiency in a main direction of incident light is the highest.

The second blazed member 104 has a second serrated surface 108 corresponding to the second serrated surface 22A. The second blazed member 104 has a second reference surface 104A. The second reference surface 104A is a virtually set surface, and for example, is a surface parallel to a surface corresponding to the concave surface 16A (refer to FIG. 1).

The second serrated surface 22A is formed with a second steep slope surface 108A and a second gentle slope surface 108B. The second gentle slope surface 108B is a surface having a gentler gradient than the second steep slope surface 108A with respect to the second reference surface 104A. The second steep slope surface 108A is perpendicular to the second reference surface 104A, and the height of the second steep slope surface 108A from the second reference surface 104A is a grating height of the second blazed member 104.

The first serrated surface 106 of the first blazed member 102 is directly engaged with the second serrated surface 108 of the second blazed member 104. In this case, the first steep slope surface 106A is in direct contact with the second steep slope surface 108A, and the first gentle slope surface 106B is in direct contact with the second gentle slope surface 108B. As shown in FIGS. 14 and 15, for convenience of description, in a case where the first steep slope surface 106A and the second steep slope surface 108A do not need to be distinguished from each other, the first steep slope surface 106A and the second steep slope surface 108A will be referred to as "steep slope surface" without being represented by reference numerals, and in a case where the first gentle slope surface 106B and the second gentle slope surface 108B do not need to be distinguished from each other, the first gentle slope surface 106B and the second gentle slope surface 108B will be referred to as "gentle slope surface" without being represented by reference numerals.

The refractive index of the first blazed member 102 is higher than the refractive index of the second blazed member 104. In the example shown in FIG. 14, "1.58" is shown as the refractive index of the first blazed member 102, and "1.56" is shown as the refractive index of the second blazed member 104.

In this case, subject light is incident from the first blazed member 102 (layer having a refractive index of "1.58") into the second blazed member 104 (layer having a refractive index of "1.56") through the gentle slope surface, is incident into the first blazed member 102 through the steep slope surface, and is incident into the second blazed member 104 through the gentle slope surface. Here, the subject light is refracted from the steep slope surface depending on an angle $\theta 1$ at which the subject light is incident into the steep slope surface. In the example shown in FIG. 14, the angle $\theta 1$ at which the subject light is incident into the steep slope surface is 5 degrees, and an angle $\theta 2$ at which the subject light is refracted from the steep slope surface is 7 degrees. As a result, in a captured image obtained by an image sensor, ghosting caused by the refraction of the subject light is imaged.

In the example shown in FIG. 14, the subject light transmitted from the first blazed member 102 through the gentle slope surface is incident into the steep slope surface. However, in the example shown in FIG. 15, the subject light incident into the first blazed member 102 is directly emitted to the steep slope surface without passing through the gentle slope surface. In this case, depending on the angle $\theta 1$, the subject light is totally reflected from the steep slope surface. For example, in a case where the angle $\theta 1$ is in a range of 0 degrees or more and 11 degrees or less, the subject light is totally reflected from the steep slope surface. As a result, in a captured image obtained by an image sensor, ghosting caused by the total reflection of the subject light is imaged.

<Details of Laminated Blazed Diffractive Optical Element>

Figure 18:
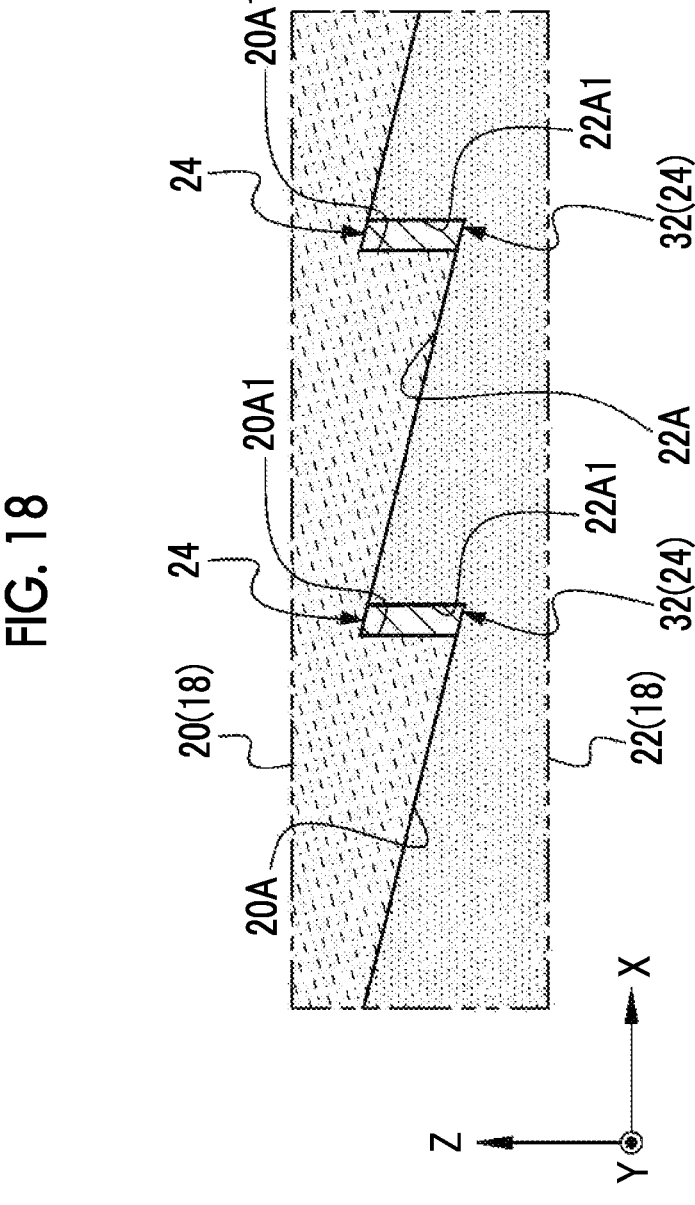
FIG. 18 is a schematic partial cross-sectional view showing a first modification example of the configuration of the laminated blazed diffractive optical element.

Under these circumstances, for example, as shown in FIG. 18, the laminated blazed diffractive optical element 12 includes the blazed diffraction grating pair 18 and the interlayer 24. The interlayer 24 having the refractive index N is positioned between the first blazed member 20 having the refractive index Na and the second blazed member 22 having the refractive index Nb. In addition, a magnitude relationship of "Na>N>Nb" is satisfied between the first blazed member 20 having the refractive index Na, the second blazed member 22 having the refractive index Nb, and the interlayer 24 having the refractive index N.

In addition, the first serrated surface 20A is formed with a first steep slope surface 20A1 and a first gentle slope surface 20A2 having a gentler gradient than the first steep slope surface 20A1. The second serrated surface 22A is formed with a second steep slope surface 22A1 and a second gentle slope surface 22A2 having a gentler gradient than the second steep slope surface 22A1. The interlayer 24 is disposed between the first steep slope surface 20A1 and the second steep slope surface 22A1 in a position between the first serrated surface 20A and the second serrated surface 22A.

In addition, the first serrated surface 20A and the second serrated surface 22A are complementarily engaged with each other through the interlayer 24. That is, the first serrated surface 20A and the second serrated surface 22A are engaged with each other through the interlayer 24 such that the first steep slope surface 20A1 and the second steep slope surface 22A1 are alternately disposed in the X direction.

In addition, the first blazed member 20 has a first reference surface 52, and the second blazed member 22 has a second reference surface 54. The first reference surface 52 and the second reference surface 54 are virtually set surfaces. The first reference surface 52 is parallel to the convex surface 14A (refer to FIG. 1), and the second reference surface 54 is parallel to the concave surface 16A (refer to FIG. 1).

The first steep slope surface 20A1 and the first gentle slope surface 20A2 are surfaces that rise from the first reference surface 52, and the second steep slope surface 22A1 and the second gentle slope surface 22A2 are surfaces that rise from the second reference surface 54. The first steep slope surface 20A1 is perpendicular to the first reference surface 52, and the second steep slope surface 22A1 is perpendicular to the second reference surface 54.

The first serrated surface 20A and the second serrated surface 22A are offset from each other by a thickness of the interlayer 24 and are engaged with each other. That is, the first serrated surface 20A and the second serrated surface 22A are engaged with each other through the interlayer 24.

In addition, a blaze angle of the first blazed member 20 and a blaze angle of the second blazed member 22 are the same. In addition, a grating height of the first blazed member 20 and a grating height of the second blazed member are the same.

For example, as shown in FIG. 17, in the laminated blazed diffractive optical element 12, in order to allow the subject light to transmit through the second blazed member 22 from the first blazed member 20 through the interlayer 24, in a case where a grating height of the first blazed member 20 and the second blazed member 22 is represented by h, a thickness of the interlayer 24 is represented by t, and a critical angle is represented by $\theta c$, the grating height h and the thickness t of the interlayer 24 are determined such that an inequality of $h<t\cdot\tan\theta$ and an equality of $\theta c=a\ \sin(Nb/Na)$ are satisfied.

The thickness t of the interlayer 24 represents the thickness between the first gentle slope surface 20A2 and the second gentle slope surface 22A2 and the thickness between the first steep slope surface 20A1 and the second steep slope surface 22A1.

In addition, here, the critical angle refers to a minimum value of an incidence angle at which transmission of the subject light from the second blazed member 22 is not allowed in a case where the subject light is emitted from the first blazed member 20 side of the laminated blazed diffractive optical element 12. Here, "the transmission of the subject light is not allowed" represents that the subject light is totally reflected, for example, between layers (media) having different refractive indices such that transmission of the subject light between the layers is not allowed. The incidence angle refers to an angle of an optical path of the subject light incident into a bonding surface between adjacent layers (for example, a bonding surface between the first blazed member 20 and the interlayer 24 and a bonding surface between the interlayer 24 and the second blazed member 22). In the example shown in FIG. 17, the angle of the optical path of the subject light incident into the bonding surface between the adjacent layers is an angle with respect to the normal line of the bonding surface.

<Action and Effect of Laminated Blazed Diffractive Optical Element>

Next, the action of the laminated blazed diffractive optical element 12 will be described.

Regarding a first medium and a second medium that satisfies a magnitude relationship of "Refractive Index of First Medium<Refractive Index of Second medium", in a case where the subject light is emitted from the second medium side to the first medium side, the subject light is totally reflected at an angle that is more than or equal to the critical angle $\theta c=a\ \sin\{(\text{Refractive Index of First Medium})/(\text{Refractive Index of Second Medium})\}$.

In the example shown in FIG. 17, the critical angle $\theta c$ between the first blazed member 20 and the interlayer 24 is more than the critical angle $\theta c$ between the first blazed member 20 and the second blazed member 22. Therefore, even in a case where the angle of the optical path of the subject light incident from the first blazed member 20 into the interlayer 24 is more than or equal to the critical angle $\theta c$ between the first blazed member 20 and the second blazed member 22, the subject light incident from the first blazed member 20 into the interlayer 24 is refracted without being totally reflected from the interlayer 24. Before arriving at the second blazed member 22, the refracted subject light arrives at a lower surface 56 (the bonding surface (boundary surface) between the interlayer 24 and the second blazed member 22) of the interlayer 24 in FIG. 17 and is incident into the second blazed member 22 adjacent to the lower surface 56.

The reason for this is that, since the grating height h and the thickness t of the interlayer 24 are determined such that an inequality of $h<t\cdot\tan\theta$ and an equality of $\theta c=a\ \sin(Nb/Na)$ are satisfied, the subject light arrives at the lower surface 56 of the interlayer 24 in the drawing before being totally reflected.

Here, in the example shown in FIG. 17, a critical angle $\theta c1$ between the first blazed member 20 and the interlayer 24 is 83.6 degrees. Therefore, in a case where the incidence angle is less than 83.6 degrees, even subject light having an incidence angle of more than 79 degrees as the critical angle θc at which the interlayer 24 is not present is not totally reflected between the first blazed member 20 and the interlayer 24. That is, in a range of 79 degrees<the angle θ<83.6 degrees, the subject light incident into the bonding surface between the first blazed member 20 and the interlayer 24 is incident into the interlayer 24 without being totally reflected from the bonding surface between the first blazed member 20 and the interlayer 24. The subject light incident into the interlayer 24 is incident from the lower surface 56 of the interlayer 24 in the drawing into the second blazed member 22.

As described above, the laminated blazed diffractive optical element 12 includes: the blazed diffraction grating pair 18 that functions as a diffraction grating with the first blazed member 20 and the second blazed member 22; and the interlayer 24 that is positioned between the first blazed member 20 and the second blazed member 22. In addition, a magnitude relationship of "Na>N>Nb" is satisfied between the first blazed member 20 having the refractive index Na, the second blazed member 22 having the refractive index Nb, and the interlayer 24 having the refractive index N. Accordingly, with the above-described configuration, ghosting caused by total reflection of incident light can be suppressed as compared to a case where the first blazed member 20 and the second blazed member 22 are directly laminated. In addition, with the above-described configuration, the distance required until light is completely refracted increases due to the presence of the interlayer 24. Therefore, the light arrives at the lower surface 56 (refer to FIG. 17) before being totally refracted, and thus ghosting caused by refraction of incident light can also be suppressed.

In addition, in the laminated blazed diffractive optical element 12, in a case where a grating height of the first blazed member 20 and the second blazed member 22 is represented by h, a thickness of the interlayer 24 is represented by t, and a critical angle is represented by θc, an inequality of h<t·tan θc and an equality of θc=a sin(Nb/Na) are satisfied. Accordingly, with the above-described configuration, the optimum grating height and the optimum thickness of the interlayer 24 where ghosting is not likely to occur can be easily determined as compared to a case where the grating height and the thickness of the interlayer 24 are determined using a condition that does not satisfy the inequality of h<t·tan θc and the equality of θc=a sin(A/C).

In addition, in the laminated blazed diffractive optical element 12, the first serrated surface 20A and the second serrated surface 22A are complementarily engaged with each other through the interlayer 24. Accordingly, with the above-described configuration, ghosting caused by incident light can be suppressed as compared to a case where the first serrated surface 20A and the second serrated surface 22A are not complementarily engaged with each other through the interlayer 24.

In addition, in the laminated blazed diffractive optical element 12, the interlayer 24 is disposed between the first steep slope surface 20A1 and the second steep slope surface 22A1 in a position between the first serrated surface 20A and the second serrated surface 22A. Accordingly, with the above-described configuration, ghosting caused by light incident into the first steep slope surface 20A1 and the second steep slope surface 22A1 can be suppressed as compared to a case where the interlayer 24 is not disposed between the first steep slope surface 20A1 and the second steep slope surface 22A1.

In addition, in the laminated blazed diffractive optical element 12, in a case where the thickness of the interlayer 24 that is disposed between the first steep slope surface 20A1 and the second steep slope surface 22A1 in the position between the first serrated surface 20A and the second serrated surface 22A is represented by t, the grating height of the first blazed member 20 and the second blazed member 22 is represented by h, and the critical angle is represented by θc, an inequality of h<t·tan θc and an equality of θc=a sin(Nb/Na) are satisfied. Accordingly, with the above-described configuration, the optimum grating height and the optimum thickness of the interlayer 24 between the first steep slope surface 20A1 and the second steep slope surface 22A1 where ghosting is not likely to occur can be easily determined as compared to a case where the grating height and the thickness of the interlayer 24 between the first steep slope surface 20A1 and the second steep slope surface 22A1 are determined using a condition that does not satisfy the inequality of h<t·tan θc and the equality of θc=a sin(A/C).

In addition, in the laminated blazed diffractive optical element 12, the first steep slope surface 20A1 is perpendicular to the first reference surface 52, and the second steep slope surface 22A1 is perpendicular to the second reference surface 54. Accordingly, with the above-described configuration, ghosting caused by light incident into the first steep slope surface 20A1 and the second steep slope surface 22A1 can be suppressed as compared to a case where the first steep slope surface 20A1 is not perpendicular to the first reference surface 52 and the second steep slope surface 22A1 is not perpendicular to the second reference surface 54.

In addition, in the laminated blazed diffractive optical element 12, the first serrated surface 20A and the second serrated surface 22A are offset from each other by a thickness of the interlayer 24 and are engaged with each other. Accordingly, with the above-described configuration, ghosting caused by incident light can be suppressed as compared to a case where the first serrated surface 20A and the second serrated surface 22A are not offset from each other by a thickness of the interlayer 24 and are not engaged with each other.

In addition, in the laminated blazed diffractive optical element 12, the interlayer 24 is formed in a film shape. Accordingly, the above-described configuration can contribute to a reduction in the thickness of the laminated blazed diffractive optical element 12.

In addition, in the laminated blazed diffractive optical element 12, a blaze angle of the first blazed member 20 and a blaze angle of the second blazed member 22 are the same. Accordingly, with the above-described configuration, ghosting caused by incident light can be suppressed as compared to a case where a blaze angle of the first blazed member 20 and a blaze angle of the second blazed member 22 are not the same.

In addition, in the laminated blazed diffractive optical element 12, a grating height of the first blazed member 20 and a grating height of the second blazed member are the same. Accordingly, with the above-described configuration, ghosting caused by incident light can be suppressed as compared to a case where a grating height of the first blazed member 20 and a grating height of the second blazed member are not the same.

In addition, the interlayer forming step in the method of manufacturing the laminated blazed diffractive optical element 12 includes a step of forming the interlayer 24 by spin coating. Accordingly, with the above-described configuration, the interlayer 24 can be easily formed in a film shape having a uniform thickness as compared to a case where the interlayer 24 is formed by vapor deposition.

In the above-described embodiment, the example where the interlayer 24 is interposed between the entire surface of the first gentle slope surface 20A2 and the entire surface of the second gentle slope surface 22A2 is described. However, the disclosed technology is not limited to this example. For example, as shown in FIG. 18, the interlayer 24 may be interposed between at least the first steep slope surface 20A1 in the first serrated surface 20A and at least the second steep slope surface 22A1 in the second serrated surface 22A. As a result, ghosting caused by light incident into the first steep slope surface 20A1 and the second steep slope surface 22A1 can be suppressed as compared to a case where the interlayer 24 is not disposed between the first steep slope surface 20A1 and the second steep slope surface 22A1.

Figure 19:
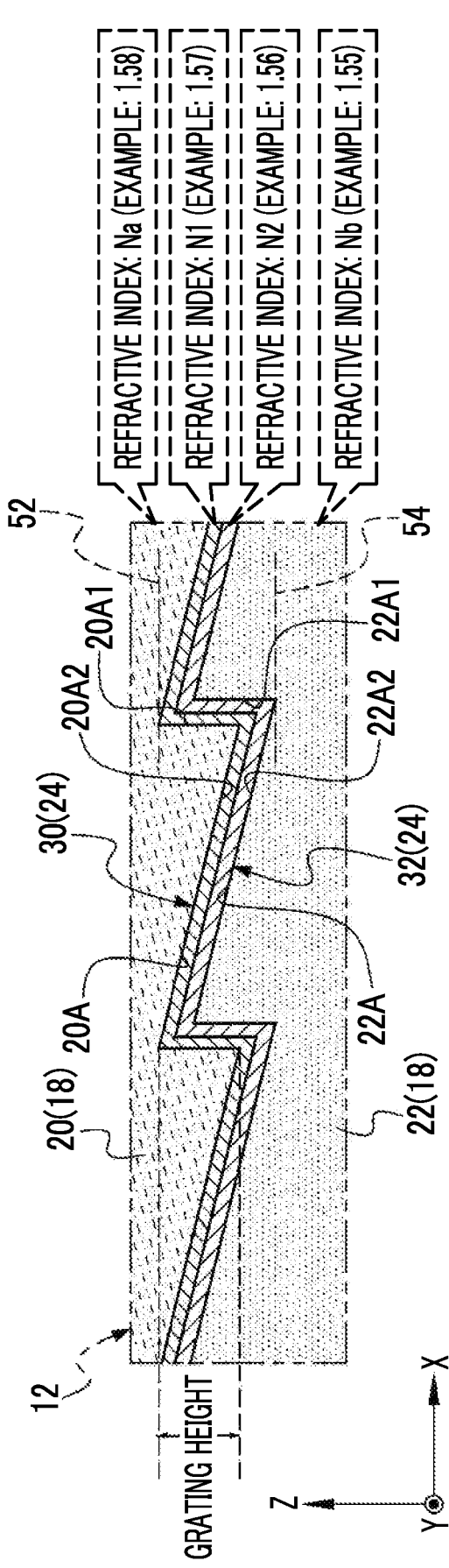
FIG. 19 is a schematic partial cross-sectional view showing a second modification example of the configuration of the laminated blazed diffractive optical element.

In addition, in the above-described embodiment, the example where the interlayer 24 is a single layer is described. However, the disclosed technology is not limited to this example, and the interlayer 24 may have a multi-layer structure. In the example shown in FIG. 19, the interlayer 24 is formed with a first layer 30 and a second layer 32. The first layer 30 and the second layer 32 are laminated. The first layer 30 is bonded to the first serrated surface 20A, and the second layer 32 is bonded to the second serrated surface 22A. That is, in a range from the convex surface 14A (refer to FIG. 1) to the concave surface 16A (refer to FIG. 1), the first blazed member 20, the first layer 30, the second layer 32, and the second blazed member 22 are laminated in this order.

Here, in a case where a refractive index of the first layer 30 is represented by N1 and a refractive index of the second layer 32 is represented by N2, a magnitude relationship of Na>N1>N2>Nb is satisfied between the refractive index Na of the first blazed member 20, the refractive index N1 of the first layer 30, the refractive index N2 of the second layer 32, and the refractive index Nb of the second blazed member. This way, in a case where the refractive index finely changes in the interlayer 24, the total reflection angle at each of interfaces increases, and thus an angle range where total reflection does not occur is widened, which is preferable. Accordingly, with the above-described configuration, the refraction of light incident into the interlayer 24 can be finely controlled stepwise as compared to a case where the interlayer 24 consists of a single layer. The first layer 30 and the second layer 32 are merely exemplary, and in a case where the interlayer 24 consists of a plurality of layers where the refractive index decreases from the first blazed member 20 side to the second blazed member 22 side, the number of the layers may be three or more. In addition, the interlayer 24 does not need to be divided into a plurality of layers, and the refractive index may continuously change.

In addition, in the above-described embodiment, the example where the ultraviolet light UV is emitted to the biconcave lens 16 through the interlayer 24 such that the second blazed member 22 and the biconcave lens 16 are integrally bonded to the interlayer 24 is described. However, the disclosed technology is not limited to this example. For example, using the cavity for molding the second blazed member 22, the second blazed member 22 may be bonded to the interlayer 24 first, and then the concave surface 16A of the biconcave lens 16 may be bonded to the second blazed member 22.

In addition, in the above-described embodiment, the example (refer to FIG. 13) where the ultraviolet light UV is emitted from the concave surface 16B side is described. However, the disclosed technology is not limited to this example. For example, the ultraviolet light UV may be emitted from the plane 14B of the plano-convex lens 14. In this case, the ultraviolet light UV having a wavelength that can transmit through the first blazed member 20 and the interlayer 24 may be emitted.

In addition, in the above-described embodiment, the ultraviolet curable resins 38, 44, 46, and 48 are described as the example. However, the disclosed technology is not limited to this example. For example, a photocurable resin that is cured by reaction with light having a wavelength different from ultraviolet light or a thermosetting resin may be used.

In addition, in the above-described embodiment, the pair of lenses are applied to the bonded optical element 10. However, the disclosed technology is not limited to this example, and an optical element other than a lens may be used as long as it is an optical element that allows transmission of light.

In addition, in the above-described embodiment, the film forming method by spin coating is described. However, the disclosed technology is not limited to this example, and a film forming method by spin coating or ink jet printing may also be used. In addition, the interlayer 24 may be formed of an inorganic material such as $SiO_2$, $TiO_2$, or $MgF_2$. In a case where the inorganic material is coated, it is preferable to use vapor deposition or the like.

In addition, in the above-described embodiment, the example where, in the plurality of layers (media) that are formed from the first blazed member 20 on the side into which the subject light is incident to the second blazed member 22, the refractive index decreases from the first blazed member 20 side to the second blazed member 22 side is described. However, the disclosed technology is not limited to this example, and the same effects as those of the embodiment can be obtained even in a case where the refractive index in the plurality of layers decreases from the second blazed member 22 side to the first blazed member 20 side irrespective of the incidence direction of the subject light.

Figure 20:
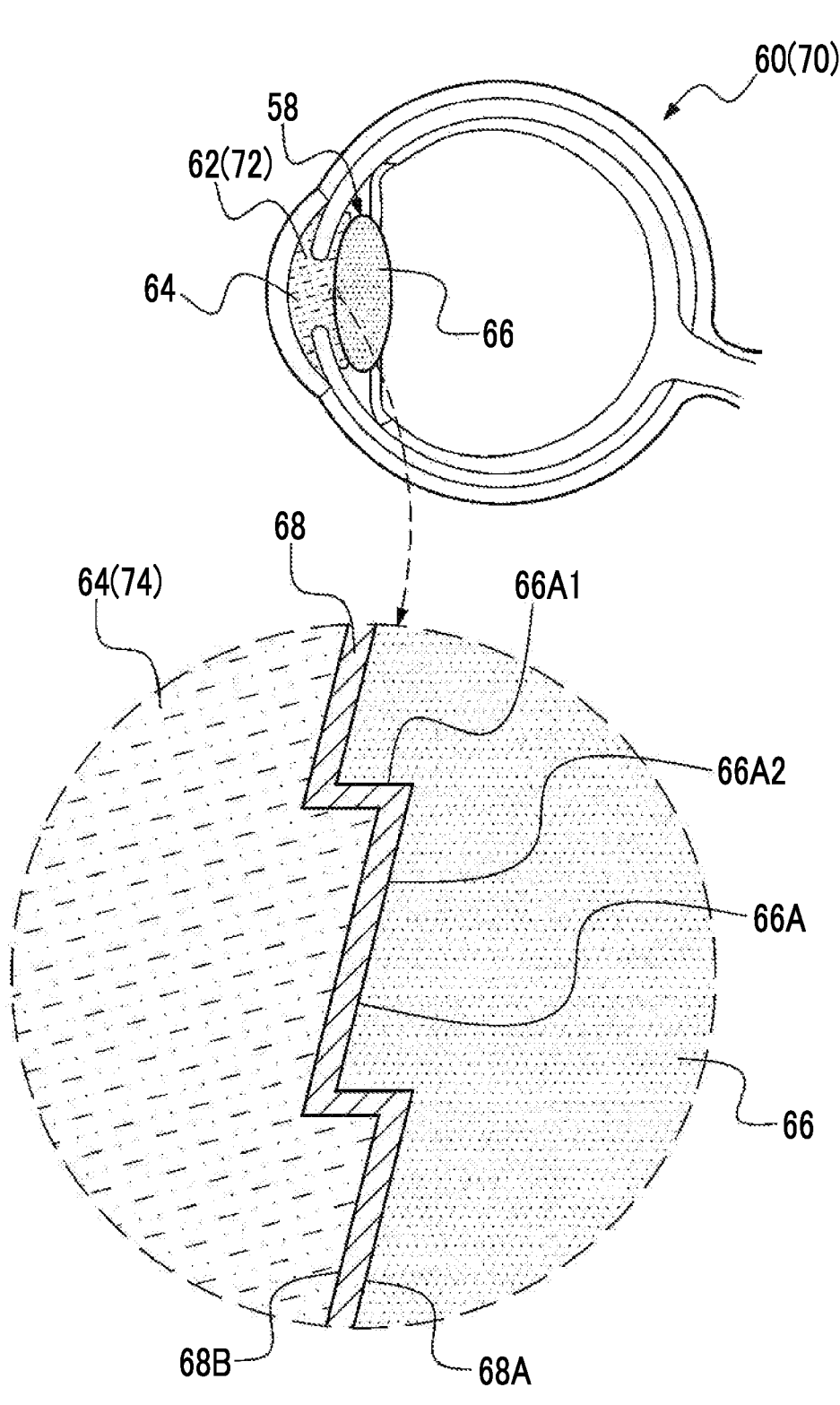
FIG. 20 is a schematic cross-sectional view showing an example of the configuration of the blazed diffractive optical element.

In addition, in the above-described embodiment, the bonded optical element 10 is described. However, the disclosed technology is not limited to this example, and the disclosed technology is also applicable to a diffractive multifocal intraocular lens. For example, as shown in FIG. 20, a diffractive multifocal intraocular lens 58 that is an example of "the blazed diffractive optical element" according to the disclosed technology is introduced into an eyeball 60 (hereinafter, also referred to as "in the eye") to be used. For example, the diffractive multifocal intraocular lens 58 may be embedded in the eye instead of the crystalline lens that becomes cloudy due to cataract. In the example shown in FIG. 20, the diffractive multifocal intraocular lens 58 is disposed instead of the crystalline lens. This way, the diffractive multifocal intraocular lens 58 is used instead of the crystalline lens. Therefore, a blazed diffraction grating is engraved on a surface (surface that comes into contact with anterior chamber aqueous humor) of the diffractive multifocal intraocular lens 58, and the surface of the diffractive multifocal intraocular lens 58 comes into direct contact with aqueous humor (hereinafter, also referred to as "anterior chamber aqueous humor") 64 filled in an anterior chamber 62.

The diffractive multifocal intraocular lens 58 may include a blazed member 66 and a surface layer 68. The blazed member 66 is a member corresponding to the second blazed member 22 described in the above-described embodiment, and the surface layer 68 is a member corresponding to the interlayer 24 described in the above-described embodiment. The surface layer 68 is an example of "the layer" according to the disclosed technology.

In the blazed member 66, a serrated surface 66A corresponding to the second serrated surface 22A described in the above-described embodiment is formed. The serrated surface 66A is formed with a steep slope surface 66A1 and a gentle slope surface 66A2. The steep slope surface 66A1 is a slope surface corresponding to the second steep slope surface 22A1 described in the above-described embodiment, and the gentle slope surface 66A2 is a slope surface corresponding to the second gentle slope surface 22A2 described in the above-described embodiment.

In the example shown in FIG. 20, a back surface 68A of the surface layer 68 is bonded to the serrated surface 66A, and a front surface 68B of the surface layer 68 is in contact with the anterior chamber aqueous humor 64. The surface layer 68 is formed in a shape corresponding to the serrated surface 66A. That is, the front surface 68B is present at a position offset from the serrated surface 66A to the anterior chamber aqueous humor 64 side by the thickness t described in the above-described embodiment, and is formed in the same shape (serrated shape) as that of the serrated surface 66A. Accordingly, a portion of the anterior chamber aqueous humor 64 that comes into contact with the front surface 68B has the same shape as the first serrated surface 20A described in the above-described embodiment.

In a case where a refractive index of the anterior chamber aqueous humor 64 is represented by A (for example, about 1.34), a refractive index of the surface layer 68 is represented by B, and a refractive index of the blazed member 66 is represented by C, the refractive index B and the refractive index C are determined such that a magnitude relationship of "A<B<C" is satisfied between the refractive index A of the anterior chamber aqueous humor 64, the refractive index B of the surface layer 68, and the refractive index C of the blazed member 66. That is, the anterior chamber aqueous humor 64 corresponds to the second blazed member 22 described in the above-described embodiment, the blazed member 66 corresponds to the first blazed member 20 described in the above-described embodiment, and the surface layer 68 corresponds to the interlayer 24 described in the above-described embodiment. Accordingly, the same effects as those of the above-described embodiment can be obtained. The surface layer 68 may also have a multi-layer structure as in the interlayer 24. In addition, the surface layer 68 does not need to be divided into a plurality of layers, and the refractive index may continuously change. For example, the surface layer 68 may have a refractive index distribution where the refractive index continuously changes from the anterior chamber aqueous humor 64 to the blazed member 66 such that the refractive index approaches the refractive index A of the anterior chamber aqueous humor 64 toward the anterior chamber aqueous humor side and the refractive index approaches the refractive index C of the surface layer 68 toward the blazed member 66.

Here, the embodiment example where the diffractive multifocal intraocular lens 58 is embedded in the eye to be used is described. However, the disclosed technology is not limited to this example. For example, the diffractive multifocal intraocular lens 58 may be applied to an eyeball model 70. In this case, a pseudo anterior chamber 72 of the eyeball model 70 may be filled with a liquid 74 having the same refractive index as the anterior chamber aqueous humor 64.

The eyeball model 70 may be used at an experimental stage for example, in a case where a device (for example, an ophthalmologic observation device or an ophthalmologic laser treatment device) used for diagnosing or treating diabetic retinopathy, retinal detachment, or the like is prepared, or may be used for skill training for a medical student or a medical doctor to perform various operations or various medical examinations.

The above-described embodiment and various modification example can be appropriately combined for the disclosed technology. In addition, the disclosed technology is not limited to the above-described embodiment, and various configurations can be adopted within a range not departing from the scope.

The contents described above and the contents shown in the drawings are the detailed description of the portions according to the disclosed technology, and are merely examples of the disclosed technology. For example, the above description regarding the configurations, the functions, the actions, and the effects are examples of the configurations, the functions, the actions, and the effects of the portions according to the disclosed technology. Accordingly, deletion of unnecessary portions, addition of new elements, or substitutions may be made for the contents described above and the contents shown in the drawings within a range not departing from the scope of the disclosed technology. Moreover, in order to avoid complications and to easily understand the portions according to the disclosed technology, common technical knowledge and the like that do not need to be described to implement the disclosed technology are not described in the contents described above and the contents shown in the drawings.

In the present specification, "A and/or B" has the same definition as "at least one of A or B". That is, "A and/or B" may be only A, may be only B, or may be a combination of A and B. In addition, in the present specification, even in a case where three or more matters are associated using "and/or" and expressed, the same way of thinking as that of "A and/or B" is applied.

All publications, patent applications, and technical standards mentioned in this specification are herein incorporated by reference to the same extent as if individual publication, patent application, or technical standard was specifically and individually indicated to be incorporated by reference.

What is claimed is:

1. A blazed diffractive optical element comprising:
a blazed diffraction grating pair that includes a first blazed member and a second blazed member and functions as a diffraction grating with the first blazed member and the second blazed member; and
an interlayer that is positioned between the first blazed member and the second blazed member,
wherein in a case where a refractive index of the first blazed member is represented by Na, a refractive index of the interlayer is represented by N, and a refractive index of the second blazed member is represented by Nb, a magnitude relationship of Na>N>Nb is satisfied,
wherein in a case where a grating height of the first blazed member and the second blazed member is represented by h, a thickness of the interlayer is represented by t, and a critical angle is represented by $\theta c$, an inequality of $h<t \cdot \tan \theta c$ and an equality of $\theta c=a \sin(Nb/Na)$ are satisfied,
wherein the first blazed member has a first serrated surface,
wherein the second blazed member has a second serrated surface,
wherein the first serrated surface and the second serrated surface are complementarily engaged with each other through the interlayer, and wherein the thickness represents a thickness between the first serrated surface and the second serrated surface, and is uniform between the first serrated surface and the second serrated surface.

2. The blazed diffractive optical element according to claim 1, wherein the first blazed member has a first serrated surface, the second blazed member has a second serrated surface, the first serrated surface is formed with a first steep slope surface and a first gentle slope surface having a gentler gradient than the first steep slope surface, the second serrated surface is formed with a second steep slope surface and a second gentle slope surface having a gentler gradient than the second steep slope surface, and the interlayer is disposed between the first steep slope surface and the second steep slope surface in a position between the first serrated surface and the second serrated surface.

3. The blazed diffractive optical element according to claim 1, wherein the first serrated surface is formed with a first steep slope surface and a first gentle slope surface having a gentler gradient than the first steep slope surface, the second serrated surface is formed with a second steep slope surface and a second gentle slope surface having a gentler gradient than the second steep slope surface, and the interlayer is disposed between the first steep slope surface and the second steep slope surface in a position between the first serrated surface and the second serrated surface.

4. The blazed diffractive optical element according to claim 1, wherein the first blazed member has a first serrated surface, the second blazed member has a second serrated surface, the first serrated surface is formed with a first steep slope surface and a first gentle slope surface having a gentler gradient than the first steep slope surface, the second serrated surface is formed with a second steep slope surface and a second gentle slope surface having a gentler gradient than the second steep slope surface, and in a case where a thickness of the interlayer that is disposed between the first steep slope surface and the second steep slope surface in a position between the first serrated surface and the second serrated surface is represented by t, a grating height of the first blazed member and the second blazed member is represented by h, and a critical angle is represented by $\theta c$, an inequality of $h < t \cdot \tan \theta c$ and an equality of $\theta c = a \sin (Nb/Na)$ are satisfied.

5. The blazed diffractive optical element according to claim 2, wherein the first blazed member has a first reference surface, the second blazed member has a second reference surface, the first steep slope surface and the first gentle slope surface are surfaces that rise from the first reference surface, the second steep slope surface and the second gentle slope surface are surfaces that rise from the second reference surface, the first steep slope surface is perpendicular to the first reference surface, and the second steep slope surface is perpendicular to the second reference surface.

6. The blazed diffractive optical element according to claim 1, wherein the first serrated surface and the second serrated surface are offset from each other by a thickness of the interlayer and are engaged with each other.

7. The blazed diffractive optical element according to claim 1, wherein the interlayer consists of a plurality of layers where a refractive index decreases from the first blazed member side to the second blazed member side.

8. The blazed diffractive optical element according to claim 1, wherein the interlayer is formed in a film shape.

9. The blazed diffractive optical element according to claim 1, wherein a blaze angle of the first blazed member and a blaze angle of the second blazed member are the same.

10. The blazed diffractive optical element according to claim 1, wherein a grating height of the first blazed member and a grating height of the second blazed member are the same.

11. A blazed diffractive optical element comprising:

a blazed member; and a layer that is provided on the blazed member, wherein a refractive index of the layer is between a refractive index of the blazed member and a refractive index of an ambient environment around the blazed member, wherein the ambient environment is anterior chamber aqueous humor in an eye, and the refractive index of the layer is between the refractive index of the blazed member and a refractive index of the anterior chamber aqueous humor, wherein in a case where the refractive index of the anterior chamber aqueous humor is represented by A, the refractive index of the layer is represented by B, and the refractive index of the blazed member is represented by C, a magnitude relationship of $A < B < C$ is satisfied, wherein the blazed member has a serrated surface, wherein the serrated surface is formed with a steep slope surface and a gentle slope surface having a gentler gradient than the steep slope surface, wherein the blazed member has a reference surface, wherein the steep slope surface and the gentle slope surface are surfaces that rise from the reference surface, wherein the steep slope surface is perpendicular to the reference surface, wherein the layer consists of a plurality of layers where a refractive index increases from the anterior chamber aqueous humor side to the blazed member side, wherein in a case where a grating height of the blazed member is represented by h, a thickness of the layer is represented by t, the thickness t is defined as a minimum normal distance between the serrated surface at the steep slope and an anterior chamber aqueous humor-side interface of the layer, and a critical angle is represented by $\theta c$, an inequality of $h < t \cdot \tan \theta c$ and an equality of $\theta c = a \sin (A/C)$ are satisfied, and wherein the thickness t represents a distance between the serrated surface and the anterior chamber aqueous humor-side interface of the layer, and is uniform between the serrated surface and the anterior chamber aqueous humor-side interface of the layer.

12. The blazed diffractive optical element according to claim 11, wherein the layer is formed on the serrated surface in a shape corresponding to the serrated surface.

13. The blazed diffractive optical element according to claim 11, wherein the serrated surface and the anterior chamber aqueous humor are offset from each other by a thickness of the layer and are in contact with each other.

14. The blazed diffractive optical element according to claim 11, wherein the layer is formed in a film shape.

15. A method of manufacturing a blazed diffractive optical element, the method comprising:

a step of forming a first blazed member;

a step of forming an interlayer on a blazed portion of the first blazed member; and a step of forming a second blazed member that is provided on a side of the interlayer opposite to the first blazed member side and forms a pair with the first blazed member, wherein in a case where a refractive index of the first blazed member is represented by Na, a refractive index of the interlayer is represented by N, and a refractive index of the second blazed member is represented by Nb, a magnitude relationship of Na>N>Nb is satisfied, wherein the step of forming the interlayer is a step of forming the interlayer by spin coating, wherein in a case where a grating height of the first blazed member and the second blazed member is represented by h, a thickness of the interlayer is represented by t, and a critical angle is represented by $\theta c$, the interlayer having a thickness that satisfies an inequality of $h < t \cdot \tan \theta c$ and an equality of $\theta c = a \sin(Nb/Na)$ is formed, wherein the thickness represents a thickness of the interlayer between the first blazed member and the second blazed member, and wherein the interlayer is formed in a film shape such that the thickness is uniform.

16. The method of manufacturing a blazed diffractive optical element according to claim 15, wherein the first blazed member has a first serrated surface, the second blazed member has a second serrated surface, and in the step of forming the second blazed member, the first serrated surface and the second serrated surface are offset from each other by a thickness of the interlayer and are engaged with each other.

* * * * *